US011617602B2

United States Patent
Rezach et al.

(10) Patent No.: US 11,617,602 B2
(45) Date of Patent: Apr. 4, 2023

(54) SYSTEMS, METHODS OF USE AND SURGICAL INSTRUMENTS EMPLOYING A SECURE SLIDE LOCK TO FASTEN A HEAD

(71) Applicant: Warsaw Orthopedic, Inc., Warsaw, IN (US)

(72) Inventors: William A. Rezach, Covington, TN (US); Daniel P. Wall, Cordova, TN (US); Abel C. Kim, Cordova, TN (US); Brian A. Butler, Millington, TN (US)

(73) Assignee: MEDTRONIC, INC., Minneapolis, MN (US)

( * ) Notice: Subject to any disclaimer, the term of this patent is extended or adjusted under 35 U.S.C. 154(b) by 151 days.

(21) Appl. No.: 17/169,920

(22) Filed: Feb. 8, 2021

(65) Prior Publication Data

US 2021/0322064 A1    Oct. 21, 2021

Related U.S. Application Data

(63) Continuation-in-part of application No. 16/850,385, filed on Apr. 16, 2020, now Pat. No. 11,439,442.

(51) Int. Cl.
*A61B 17/70* (2006.01)
*A61B 17/02* (2006.01)

(52) U.S. Cl.
CPC .. *A61B 17/7074* (2013.01); *A61B 2017/0256* (2013.01)

(58) Field of Classification Search
CPC ............................................ A61B 17/72–7291
See application file for complete search history.

(56) References Cited

U.S. PATENT DOCUMENTS

| 6,530,929 | B1 | 3/2003 | Justis et al. |
| 6,565,568 | B1 | 5/2003 | Rogozinski |
| 7,670,358 | B2 | 3/2010 | Barry |
| 7,749,233 | B2 | 7/2010 | Farr et al. |
| 7,776,072 | B2 | 8/2010 | Barry |

(Continued)

OTHER PUBLICATIONS

"CD Horizon Solera 5.5/6.0 Spinal System, Surgical Technique," www.medtronic.com <http://www.medtronic.com>, Medtronic Inc., copyright 2014.

(Continued)

*Primary Examiner* — Eduardo C Robert
*Assistant Examiner* — Steven J Cotroneo
(74) *Attorney, Agent, or Firm* — Fox Rothschild LLP

(57) ABSTRACT

A system comprising surgical instruments of different types. Each surgical instrument includes a body member and a leg having a first end integrated with and a leg portion extending from the body member. The instrument includes a head cavity formed in a free end of the leg. The cavity holds a head. A channel is formed along a portion of a longitudinal length of the leg. The instrument includes an elongated rocker assembly pivotally coupled within the channel, with a spring actuation tab in proximity to the body member. The instrument includes a collar slidably coupled around the body member and having a first position located between the body member and the actuation tab such that a portion of the collar is under the actuation tab to limit pivotal motion of the rocker assembly and a second position of the collar has a clearance from under the actuation tab.

21 Claims, 23 Drawing Sheets

(56) References Cited

U.S. PATENT DOCUMENTS

| | | | |
|---|---|---|---|
| 7,951,168 B2 | 5/2011 | Chao et al. | |
| 7,951,175 B2 | 5/2011 | Chao et al. | |
| 8,007,516 B2 | 8/2011 | Chao et al. | |
| 8,038,699 B2 | 10/2011 | Cohen et al. | |
| 8,162,952 B2 * | 4/2012 | Cohen | A61B 17/708 |
| | | | 606/104 |
| 8,187,334 B2 | 5/2012 | Curran et al. | |
| 8,211,110 B1 | 7/2012 | Corin et al. | |
| 8,394,109 B2 * | 3/2013 | Hutton | A61B 17/7083 |
| | | | 606/105 |
| 8,535,318 B2 | 9/2013 | Peterson et al. | |
| 8,591,515 B2 * | 11/2013 | Jackson | A61B 17/7002 |
| | | | 606/86 A |
| 8,623,022 B2 | 1/2014 | Forton et al. | |
| 8,709,044 B2 | 4/2014 | Chao et al. | |
| 8,795,283 B2 | 8/2014 | Petit | |
| 8,821,502 B2 | 9/2014 | Gleeson et al. | |
| 8,845,649 B2 | 9/2014 | Jackson | |
| 8,876,835 B2 | 11/2014 | Petit | |
| 8,900,240 B2 | 12/2014 | White et al. | |
| 8,906,034 B2 | 12/2014 | Gleeson et al. | |
| 8,936,605 B2 | 1/2015 | Greenberg | |
| 9,011,447 B2 * | 4/2015 | Arnett | A61B 17/86 |
| | | | 606/279 |
| 9,125,694 B2 | 9/2015 | Butler et al. | |
| 9,155,573 B2 * | 10/2015 | May | A61B 17/7077 |
| 9,179,957 B2 | 11/2015 | Ibrahim et al. | |
| 9,241,742 B2 | 1/2016 | Stad | |
| 9,271,767 B2 | 3/2016 | Jackson | |
| 9,314,273 B2 | 4/2016 | Iott et al. | |
| 9,314,280 B2 | 4/2016 | Corin | |
| 9,320,550 B2 | 4/2016 | Hutton et al. | |
| 9,351,770 B2 | 5/2016 | Sharps | |
| 9,402,662 B2 | 8/2016 | Mahar | |
| 9,402,663 B2 | 8/2016 | Peterson et al. | |
| 9,480,500 B2 | 11/2016 | Ibrahim et al. | |
| 9,480,504 B1 | 11/2016 | Schafer et al. | |
| 9,510,875 B2 | 12/2016 | Reitblat et al. | |
| 9,532,815 B2 | 1/2017 | Jackson | |
| 9,603,628 B2 | 3/2017 | Butler et al. | |
| 9,629,667 B2 | 4/2017 | Petit | |
| 9,642,654 B2 | 5/2017 | Reimels et al. | |
| 9,668,776 B2 | 6/2017 | Ibrahim et al. | |
| 9,808,281 B2 | 11/2017 | Solitario, Jr. et al. | |
| 9,877,750 B2 | 1/2018 | Iott et al. | |
| 9,936,986 B2 | 4/2018 | Butler et al. | |
| 9,968,384 B2 | 5/2018 | Fischer et al. | |
| 9,968,394 B2 * | 5/2018 | Meyer | A61B 17/8863 |
| 9,999,448 B2 | 6/2018 | Stad | |
| 10,028,773 B2 | 7/2018 | Ibrahim et al. | |
| 10,034,695 B1 | 7/2018 | Schafer et al. | |
| 10,052,140 B2 | 8/2018 | Krause et al. | |
| 10,085,807 B2 | 10/2018 | Butters et al. | |
| 10,219,845 B2 | 3/2019 | Petit | |
| 10,258,390 B2 | 4/2019 | Biedermann et al. | |
| 10,314,624 B2 | 6/2019 | Chao et al. | |
| 10,441,328 B2 | 10/2019 | Petit | |
| 10,499,952 B2 | 12/2019 | Iott et al. | |
| 10,568,669 B2 | 2/2020 | Reitblat et al. | |
| 10,595,912 B2 | 3/2020 | Krause et al. | |
| 2003/0065328 A1 | 4/2003 | Shevtsov et al. | |
| 2005/0085813 A1 | 4/2005 | Spitler et al. | |
| 2005/0245928 A1 | 11/2005 | Colleran et al. | |
| 2008/0015601 A1 | 1/2008 | Castro et al. | |
| 2008/0077134 A1 * | 3/2008 | Dziedzic | A61B 17/8875 |
| | | | 606/68 |
| 2010/0004695 A1 * | 1/2010 | Stad | A61B 17/708 |
| | | | 606/86 A |
| 2011/0166606 A1 * | 7/2011 | Stihl | A61B 17/7086 |
| | | | 606/279 |
| 2012/0265212 A1 * | 10/2012 | Seck | A61B 17/708 |
| | | | 606/86 A |
| 2012/0283786 A1 * | 11/2012 | Rezach | A61B 17/7086 |
| | | | 606/305 |
| 2013/0012999 A1 * | 1/2013 | Petit | A61B 50/33 |
| | | | 606/279 |
| 2013/0018419 A1 * | 1/2013 | Rezach | A61B 17/7076 |
| | | | 606/264 |
| 2013/0184763 A1 * | 7/2013 | McClintock | A61B 17/708 |
| | | | 606/279 |
| 2013/0211453 A1 * | 8/2013 | Lenke | A61B 17/7077 |
| | | | 606/250 |
| 2014/0188182 A1 | 7/2014 | Chao et al. | |
| 2014/0277200 A1 * | 9/2014 | Parker | A61B 17/7038 |
| | | | 606/86 A |
| 2015/0051648 A1 * | 2/2015 | May | A61B 17/7086 |
| | | | 606/264 |
| 2015/0164569 A1 * | 6/2015 | Reitblat | A61B 17/708 |
| | | | 606/279 |
| 2016/0310174 A1 | 10/2016 | Peterson et al. | |
| 2017/0049428 A1 * | 2/2017 | Cryder | A61B 17/0206 |
| 2017/0079696 A1 | 3/2017 | Walker et al. | |
| 2017/0112551 A1 | 4/2017 | Suh et al. | |
| 2017/0311980 A1 | 11/2017 | Solitario, Jr. et al. | |
| 2018/0185072 A1 | 7/2018 | Rubin et al. | |
| 2018/0235676 A1 | 8/2018 | Butler et al. | |
| 2019/0008565 A1 | 1/2019 | Peterson et al. | |
| 2019/0021772 A1 | 1/2019 | Schafer et al. | |
| 2019/0069934 A1 * | 3/2019 | Mickiewicz | A61B 17/861 |
| 2019/0090908 A1 | 3/2019 | Stad | |
| 2019/0142471 A1 | 5/2019 | Lindner | |
| 2019/0307492 A1 | 10/2019 | Chao et al. | |
| 2019/0336182 A1 | 11/2019 | Suh et al. | |
| 2020/0069338 A1 | 3/2020 | Iott et al. | |
| 2020/0305932 A1 * | 10/2020 | Park | A61B 17/7091 |

OTHER PUBLICATIONS

"Deformity Procedural Solutions, AIS Procedural Solutions," www.medtronic.com <http://www.medtronic.com>, Medtronic Inc., copyright 2018.

Olerud et al., Transpedicular Fixation of Thoracolumbar Vertebral Fractures, Clinical Orthopaedics and Related Research 227:44-51 (1988).

* cited by examiner

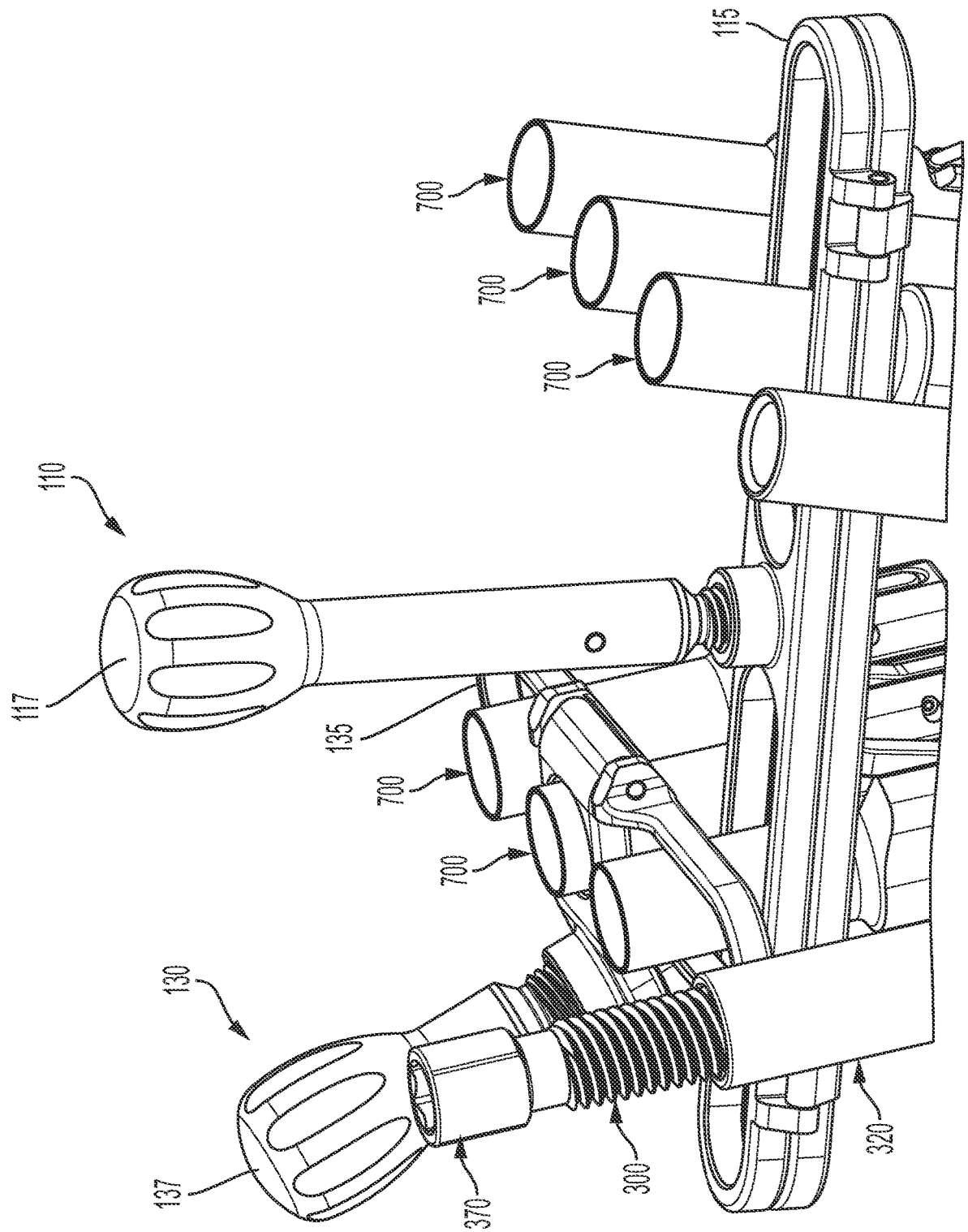

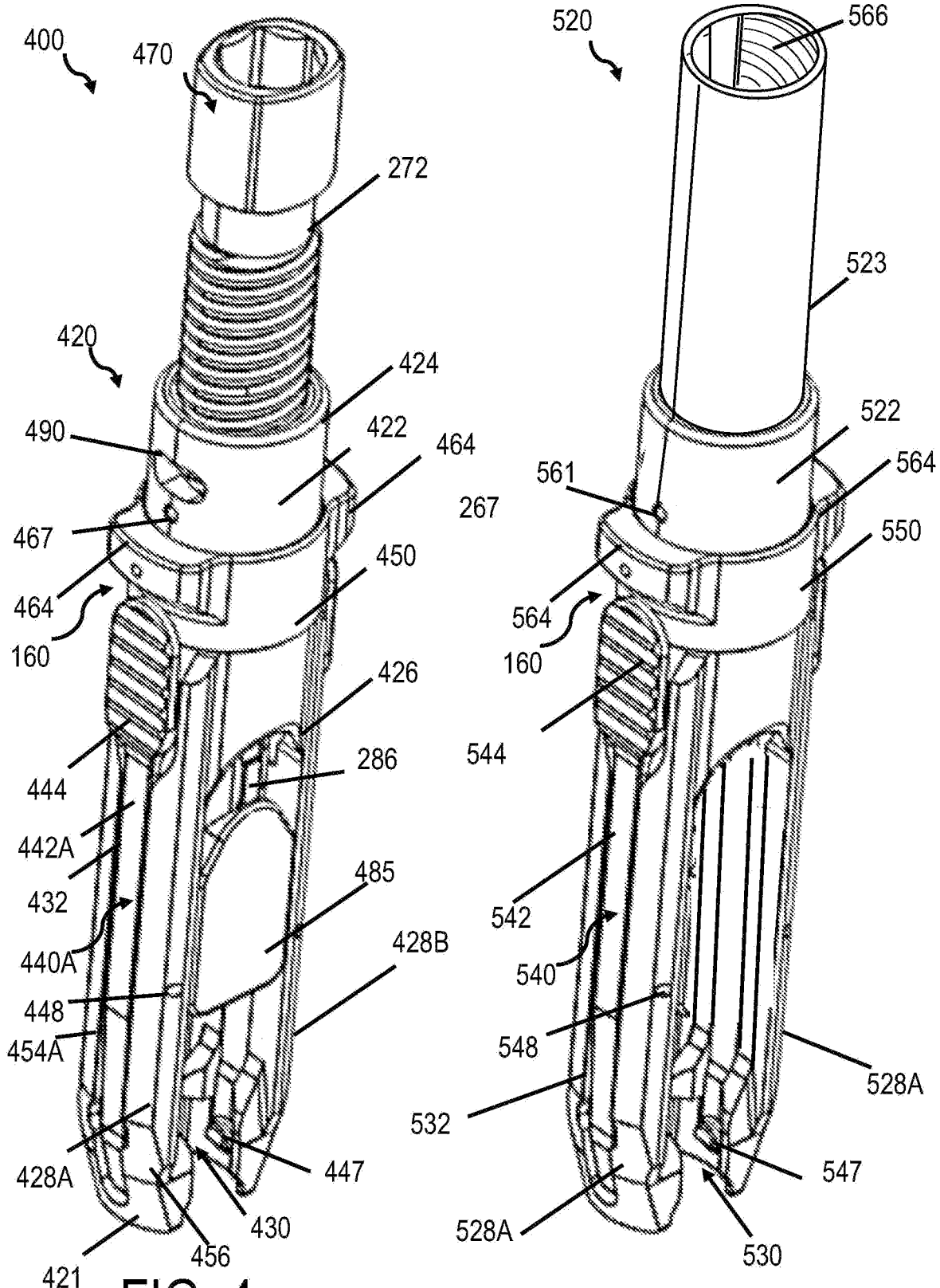

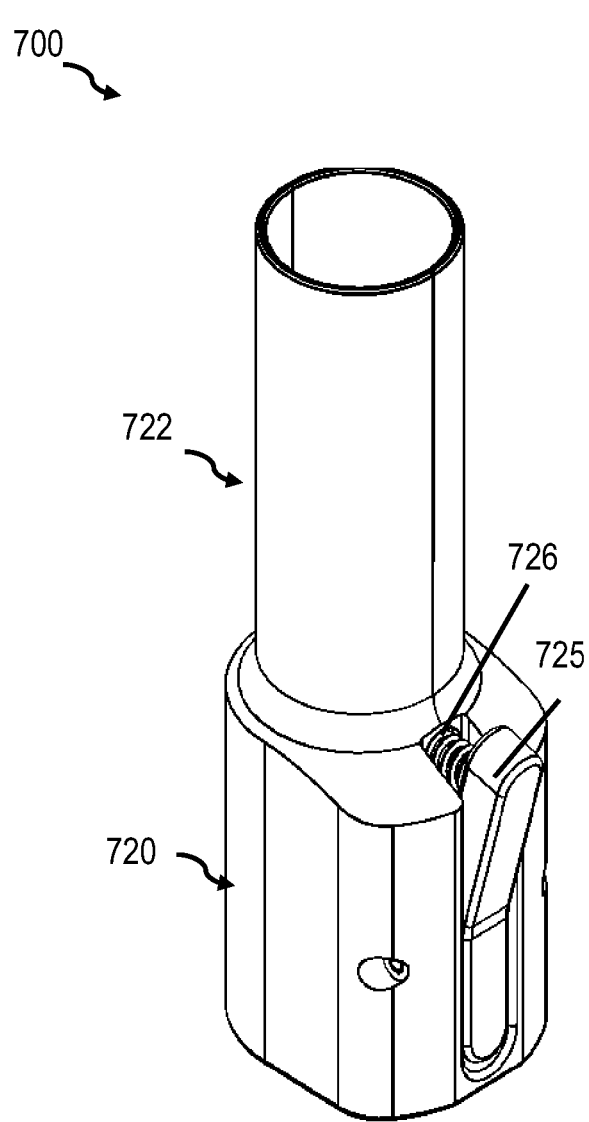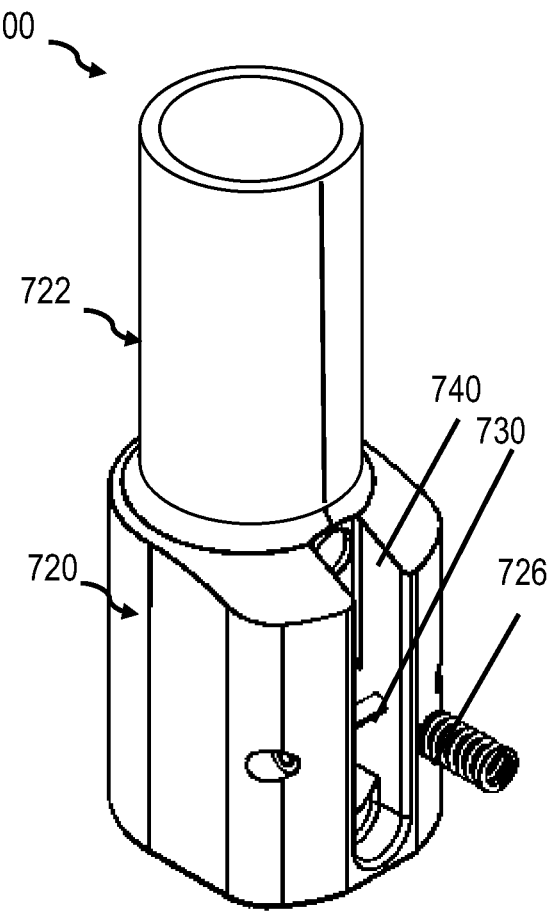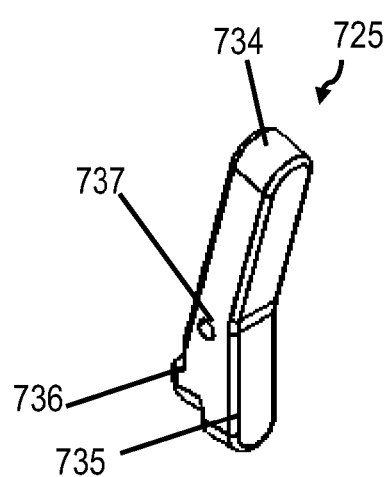
FIG. 7A
FIG. 7B

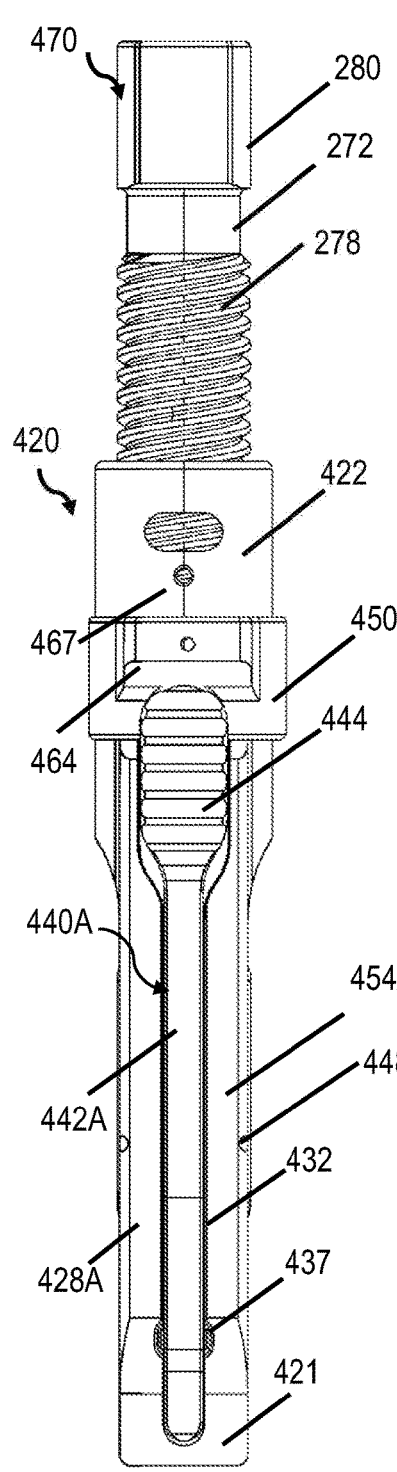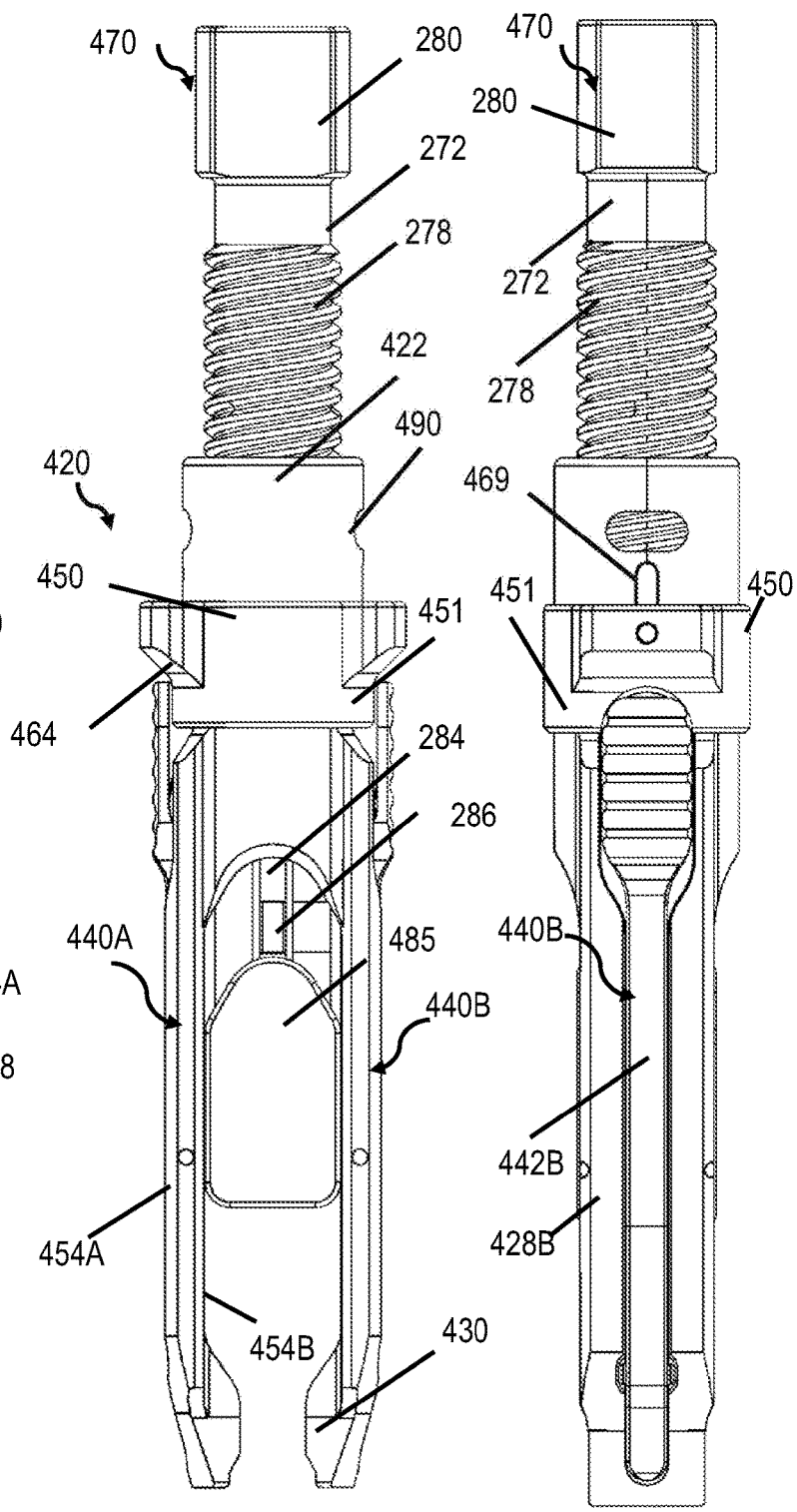
FIG. 16A  FIG. 16B  FIG. 16C

SYSTEMS, METHODS OF USE AND SURGICAL INSTRUMENTS EMPLOYING A SECURE SLIDE LOCK TO FASTEN A HEAD

CROSS-REFERENCE TO RELATED APPLICATIONS

This application is a continuation-in-part of U.S. application Ser. No. 16/850,385, filed Apr. 16, 2020, which is incorporated herein by reference in its entirety.

FIELD

The present technology is generally related systems and methods of use and surgical instruments such as extenders and derotators that secure spinal constructs including bone fasteners and connectors for treating the spine.

BACKGROUND

Spinal disorders of the spine may result in symptoms, such as without limitation, nerve damage, and partial or complete loss of mobility and chronic pain. Surgical treatment of these spinal disorders includes correction, fusion, fixation, discectomy, laminectomy and implantable prosthetics, for example. As part of these surgical treatments, vertebral rods and bone fasteners are often used to provide stability to a treated region. During surgical treatment, a surgeon uses various surgical instruments, such as extenders, reducers and derotators, to implant one or more rods and bone fasteners to a surgical site. Extenders, for example, are used with reducers to implant a rod.

This disclosure describes an improvement over these prior art technologies.

SUMMARY

The techniques of this disclosure generally relate, for example, to systems and method, for example, using instruments with a rocker slide lock that when locked and/or connected reduces the likelihood of and/or prevents a head-locking projection for securing a head of the bone fastener from becoming inadvertently disengaged. The surgical instrument's configuration may maintain a minimum profile as the elongated rocker assembly is moved into an engaged position and/or disengaged position.

In one aspect, the present disclosure provides a system that may include a plurality of surgical instruments of different types. Each surgical instrument may include a body member having a top end and a bottom end. Each instrument may include a leg having a first end integrated with and a leg portion extending from the body member. A head cavity may be formed in the leg portion and may be configured to hold a head. Each instrument may include an elongated channel formed along the leg and an elongated rocker assembly pivotally coupled within the channel, with a spring actuation tab in proximity to the body member. A collar may be slidably coupled around the body member. The collar may include a first position located between the body member and the actuation tab such that a portion of the collar may be under the actuation tab to limit pivotal motion of the rocker assembly and a second position of the collar has a clearance from under the actuation tab.

In various aspects, the instruments may include reducers of different sizes. The instruments may include a derotator.

In another aspect, the disclosure provides a method that may include providing a plurality of reducers and coupling a respective one reducer to a respective one surgical instrument to form an instrument assembly with a rocker slide lock. The method may include using the instrument assembly for reducing a rod in a head of a bone fastener and prior to reducing the rod, locking and/or connecting the head with rocker slide lock.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 1B is a perspective view that illustrates some components of the universal surgical implant system being linked together.

FIG. 4 is a perspective view that illustrates a short closed-extender instrument assembly.

FIG. 5 is a perspective view that illustrates a long closed-extender.

FIG. 7A is a perspective view that illustrates a short instrument adapter.

FIG. 7B is a perspective view that illustrates a short instrument adapter with the lever and spring separated.

FIGS. 16A-16C are front, side and rear views of the short closed-extender instrument assembly of FIG. 4.

DETAILED DESCRIPTION

Figure 1A:
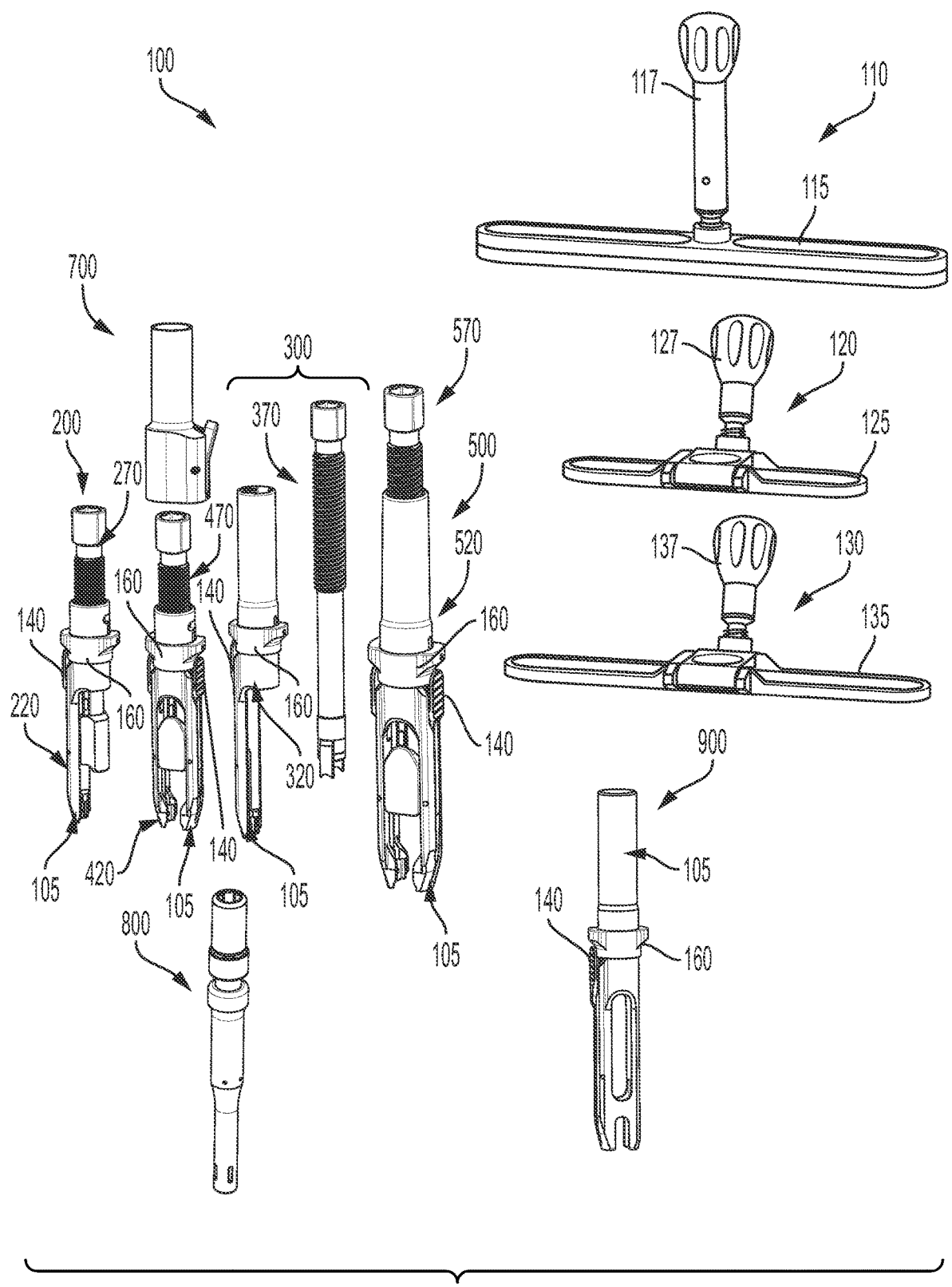
FIG. 1A is a perspective view that illustrates components of universal surgical implant system.

The embodiments of the universal surgical implant system are discussed in terms of medical devices for the treatment of musculoskeletal disorders and more particularly, in terms of a surgical system and a method for treating a spine. In the embodiments, the system may include a surgical instrument that may include a rocker slide lock to, for example, lock a head-locking projection in a bone fastener nestled in the head cavity, and the related methods of use that can be employed with spinal constructs including bone fasteners and connectors that provide a universal surgical implant system for spine surgeons. The rocker slide lock when locked may, for example, reduce the likelihood of or prevent a head-locking projection for securing a head (e.g., polyaxial head, uni-axial head, monoaxial head, etc.) of the bone fastener from becoming inadvertently disengaged. The surgical instrument's configuration may maintain a minimum profile as the elongated rocker assembly is moved into an engaged position and/or disengaged position.

In some embodiments, the system may include an extender and derotator that are configured with a rocker slide lock to lock and/or connect a head-locking projection in a head (e.g., polyaxial head, uni-axial head, monoaxial head, etc.) of a bone fastener nestled in the head cavity, and the related methods of use that can be employed with spinal constructs including bone fasteners and connectors that provide a universal surgical implant system for spine surgeons. The extender's configuration and derotator's configuration maintain a minimum profile as the elongated rocker assembly is moved into an engaged position and/or a disengaged position.

In some embodiments, the system may include different types and sizes of extenders and an adapter for each extender of a first size, and the related methods of use that can be employed with segmental links and interlinks to provide a universal surgical implant system for spine surgeons.

The system of the present disclosure may be understood more readily by reference to the following detailed description of the embodiments taken in connection with the accompanying drawing figures that form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, front, back, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of and/or reducing the likelihood of a certain disease or undesirable condition (e.g., preventing or reducing the likelihood of the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a surgical instrument, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIG. 1A, components of a universal surgical implant system 100 are illustrated, in accordance with the principles of the disclosure.

The components of system 100 can be fabricated from biologically acceptable materials suitable for medical applications, including metals, synthetic polymers, ceramics and bone material and/or their composites. For example, the components of system 100, individually or collectively, can be fabricated from materials such as stainless steel alloys, aluminum, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologic Inc.), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of system 100 may have material composites, including the above materials, to achieve various desired characteristics such as strength, rigidity, elasticity, compliance, biomechanical performance, durability and radiolucency or imaging preference. The components of system 100, individually or collectively, may also be fabricated from a heterogeneous material such as a combination of two or more of the above-described materials. The components of system 100 may be monolithically formed, integrally connected or include fastening elements and/or instruments, as described herein.

The system 100 may include at least one surgical instrument 105 and be employed, for example, with an open or mini-open, minimal access and/or minimally invasive including percutaneous surgical technique to deliver and fasten an implant at a surgical site within a body of a patient, for example, a section of a spine. In one embodiment, the components of system 100 may be configured to implant and/or fix a bone fastener, such as a pedicle screw, or other implants within tissue for a surgical treatment to treat various spine pathologies, such as those described herein.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

FIG. 1A is a perspective view that illustrates components of universal surgical implant system 100. A surgeon when performing surgical deformity procedures may need to manipulate the spine (i.e., derotation) and reduce the spinal curvature using an elongated rod to be put in place using at least one surgical instrument 105 such as, without limitation, an extender and/or a derotator. The system 100 may include an extender and/or a derotator, each with a rocker slide lock 160 and an elongated rocker assembly 140 may be constructed and arranged to lock/connect a head-locking projection 247 (FIG. 15) of the rocker assembly 140 in a bone fastener (not shown) nestled in a head cavity. The arrangement of the rocker slide lock 160 and elongated rocker assembly 140 prevents and/or reduces the likelihood of the head-locking projection 247 from becoming inadvertently disengaged from the bone fastener. The system 100 may employ other tools, fasteners, such as described in "CD Horizon® Solera® 5.5/6.0 Spinal System," by Medtronic, Inc., copyright date 2014, which is incorporated herein by reference in its entirety.

The system 100 may include different types and sizes of instruments, such as without limitation, open-extender types, closed-extender types, short extender types and long extender types. For example, the system 100 may include one or more short open-extender instrument assemblies 200 that may include a short open-extender 220 and a short reducer 270, as will be described in more detail in relation to FIG. 2. The system 100 may include one or more long open-extender instrument assemblies 300 that may include a long open-extender 320 and a long reducer 370, as will be described in more detail in relation to FIG. 3. The system 100 may include one or more short closed-extender instrument assemblies 400 that may include a short closed-extender 420 and a short reducer 470, as will be described in more detail in relation to FIG. 4. The system 100 may include one or more long closed-extender instrument assemblies 500 that may include a long closed-extender 520 and a long reducer 570, as will be described in more detail in relation to FIG. 5.

The system 100 may include one or more short instrument adapters 700, as will be described in more detail in relation to FIG. 7. The short instrument adapter 700 is use with the short type extenders such as a short open-extender 220 and a short closed-extender 420. The system 100 may include one or more shank-extender instrument assemblies 800, as will be described in more detail in relation to FIGS. 8A-8B. The system 100 may include one or more derotators 900, as will be described in more detail in relation to FIG. 9.

Referring also to FIG. 1B, a perspective view that illustrates some components of the universal surgical implant system 100 being linked together is shown. The system 100 may include one or more segmental link assemblies 110 and first and second interlink assemblies 120 and 130. The segmental link assembly 110 may include a segmental link 115 and a handle 117 configured to attach to the segmental link. The first interlink assembly 120 may include interlink element 125 with a handle 127 configured to attach to the interlink element 125. The second interlink assembly 130 may include interlink element 135 with a handle 137 configured to attach to the interlink element 135. In some embodiments, the interlink element 125 may have a different size than the interlink element 135. The interlink elements and segmental link may be generally elliptically shaped.

In some embodiments, an interlink element 125 or 135 may be installed on at least one short open-extender instrument assembly 200, at least one short closed-extender instrument assembly 400 or a combination of short open-extender instrument assemblies 200 and short closed-extender instrument assemblies 400 via the short instrument adapters 700. Although the short extender type surgical instruments have different configuration, the short instrument adapters 700 provides a universal connection for such short type extenders. The segmental link assemblies 110 and first and second interlink assemblies 120 and 130 may be described in U.S. patent application Ser. No. 17/167,415, titled "SURGICAL INSTRUMENT AND METHOD," incorporated herein by reference in its entirety. Examples of other segmental link assemblies 110 and the first and second interlink assemblies 120 and 130 are also, for example, described in "CD Horizon® Solera® 5.5/6.0 Spinal System," by Medtronic, Inc., copyright date 2014.

Figure 2:
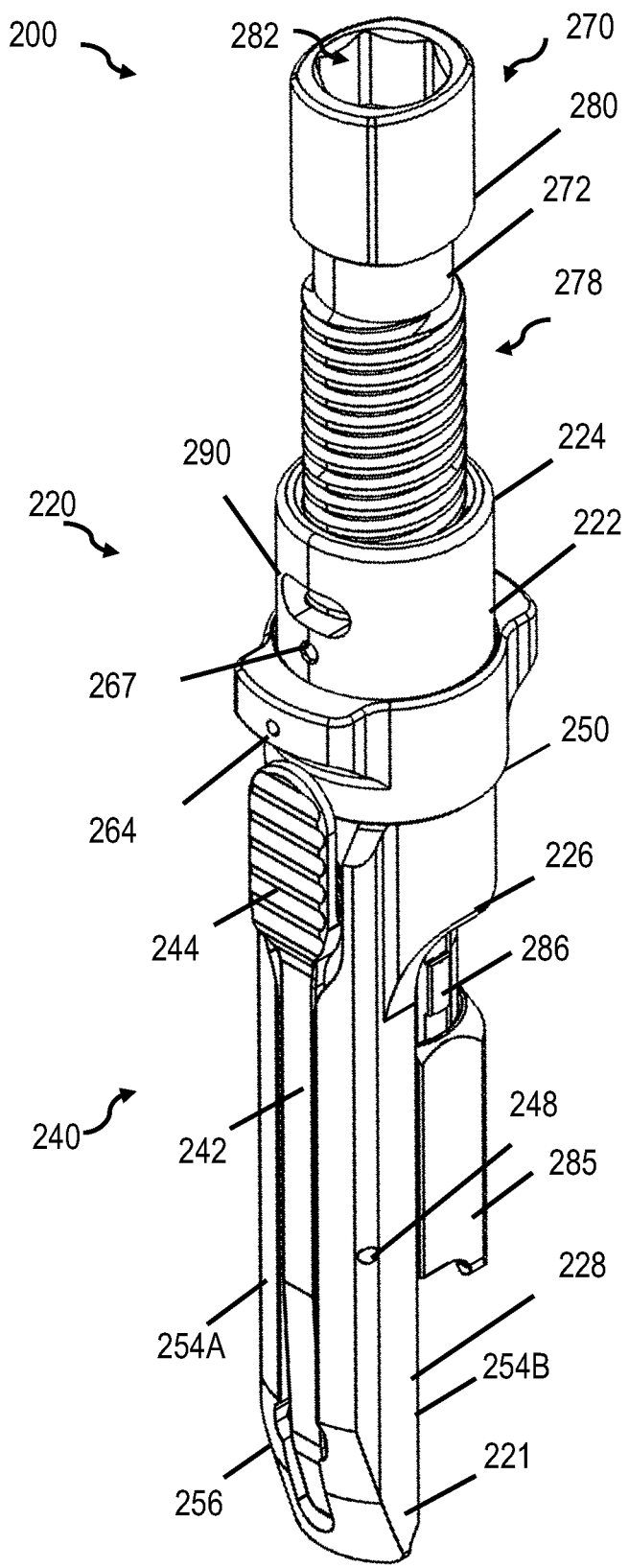
FIG. 2 is a perspective view that illustrates a short open-extender instrument assembly.
Figure 10A:
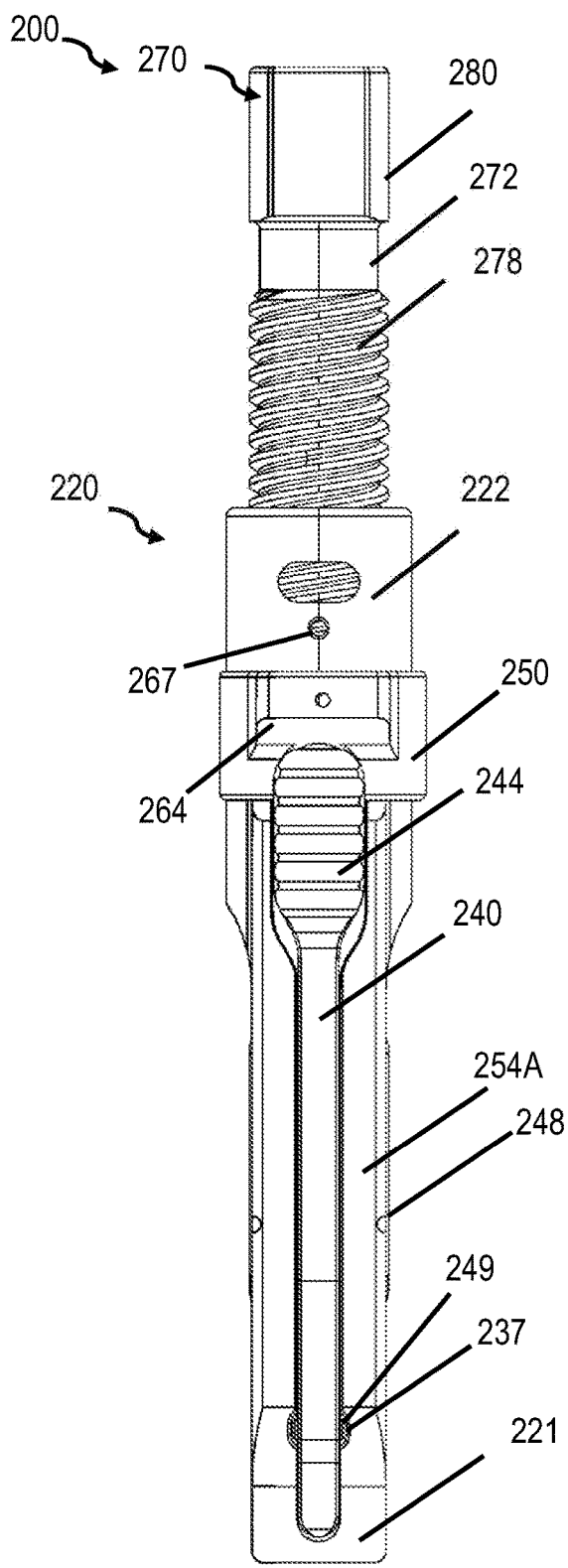
FIGS. 10A-10B are front and back views that illustrate the short open-extender instrument assembly of FIG. 2.
Figure 10B:
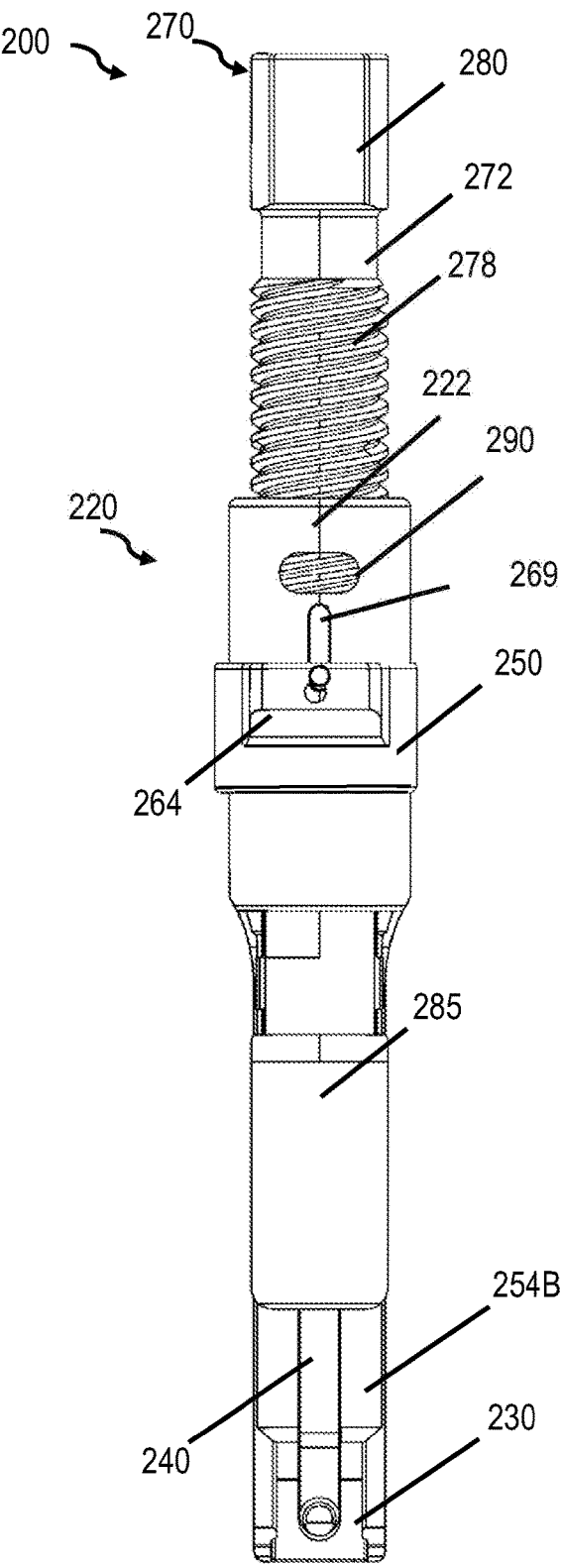
Figure 11A:
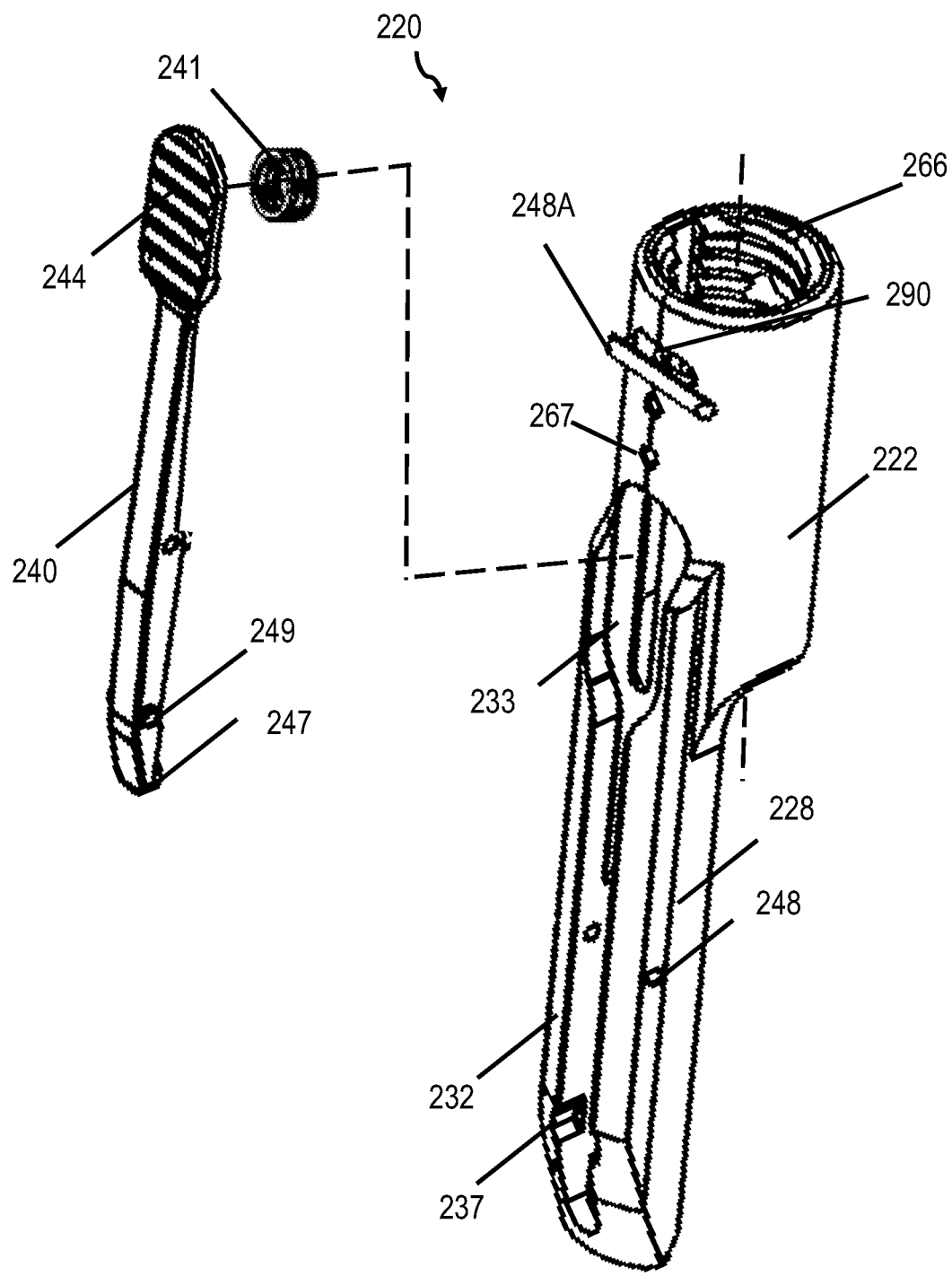
FIGS. 11A-11B are perspective views that together illustrate an exploded view of the short open-extender instrument assembly of FIG. 2.
Figure 11B:
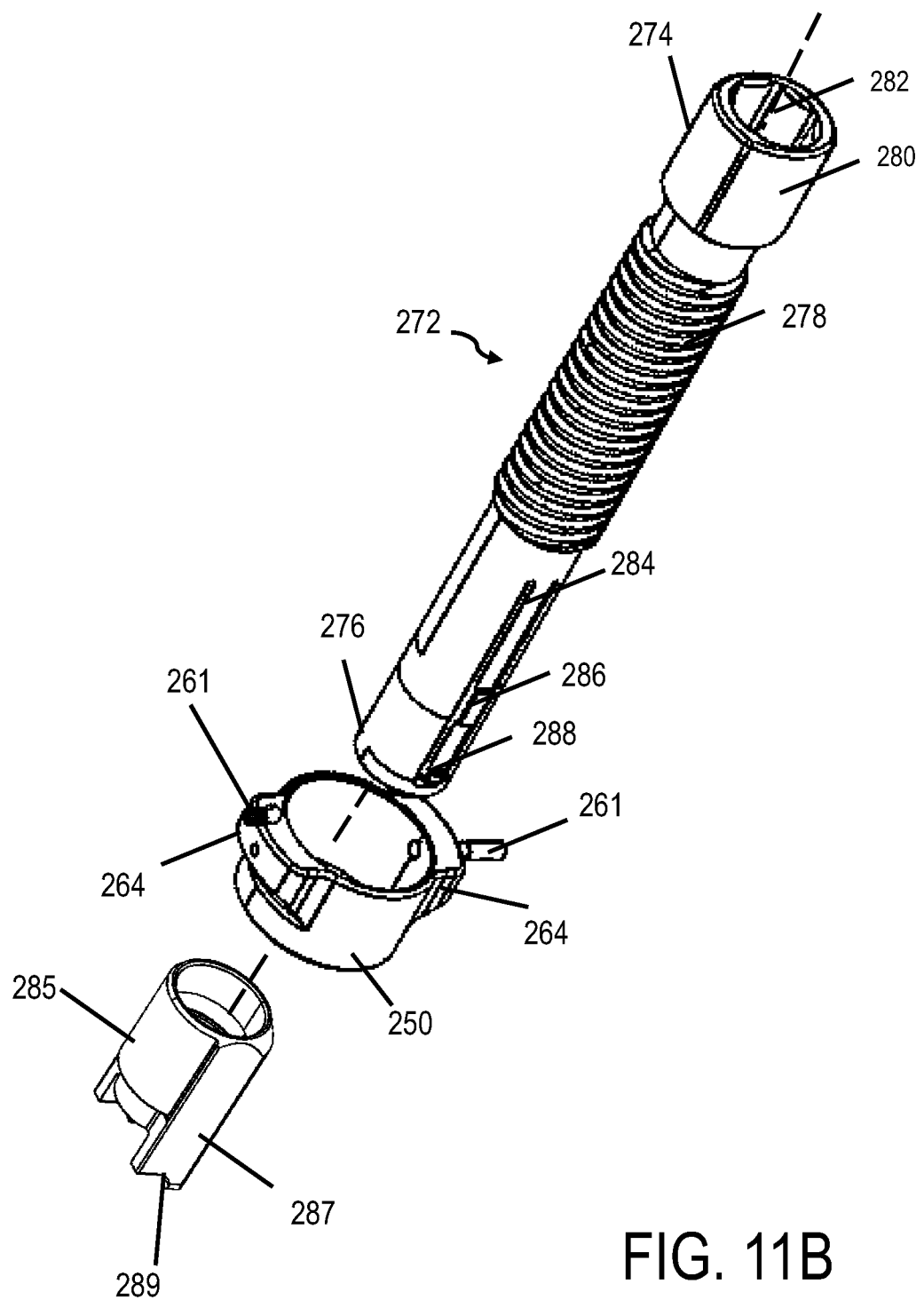
Figure 11C:
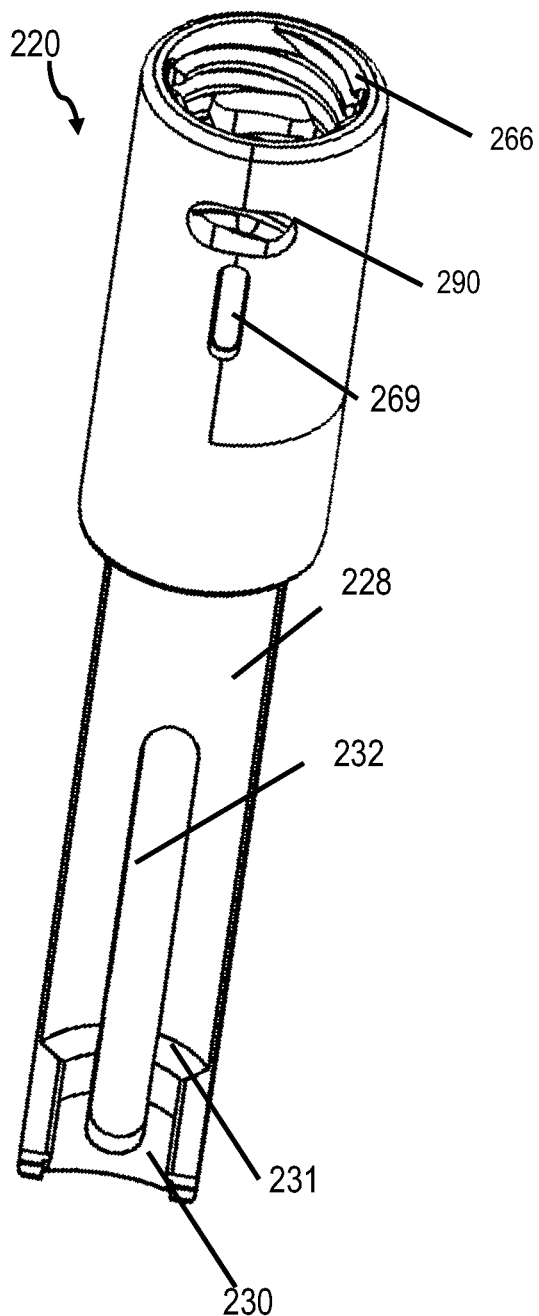
FIG. 11C is a perspective view that illustrates a rear side of the short closed-extender.

FIG. 2 is a perspective view that illustrates a short open-extender instrument assembly 200. The short open-extender instrument assembly 200 may include a short open-extender 220 and a short reducer 270. The short open-extender instrument assembly 200 of FIG. 2 will also be described in relation to FIGS. 10A-10B, 11A-11C, 12A-12B, and 13. Specifically, FIGS. 10A-10B are front and back views that illustrate the short open-extender instrument assembly 200 of FIG. 2. FIG. 11A-11B are perspective views that together illustrate an exploded view of the short open-extender instrument assembly 200 of FIG. 2. FIG. 11C is a perspective view that illustrates a rear side of the short closed-extender.

The short open-extender 220 may include a body member 222 having a top end 224 and a bottom end 226. The short open-extender 220 may include a leg 228 having a first end integrated with and a leg portion extending from the body member 222.

The short open-extender 220 may include a head cavity 230 (FIG. 10B) formed in a free end 221 of the leg 228 and configured to hold a head (not shown). The head cavity 230 may include a top surface 231 (FIG. 11C). A leg 228 may include an elongated channel 232 (FIG. 11A, 11C) that may be formed along a portion of a longitudinal length of the leg 228. The channel 232 may include an elongated hole in the leg 228. The channel 232 may include a seat 233 integrated with the body member 222. The short open-extender 220 may include at least one adapter fastening element 290 formed in body member 222.

The short open-extender 220 may include an elongated rocker assembly 240 pivotally coupled within the channel 232 (FIG. 11A, 11C), with an actuation tab 244 and spring 271 in proximity to the body member 222. The seat 233 forms a recess dimensioned to conform to the profile of the actuation tab 244. The spring 271 is adapted to be position between the seat 233 and a medial side of the actuation tab 244. The short open-extender 220 may include a collar 250 slidably coupled around the body member 222. A center axis of the collar 250 may be configured to align with a longitudinal axis of the body member 222.

FIG. 11A illustrates a lateral side of channel 232. FIG. 11C illustrates a medial side of the channel 232. The lateral side of the channel 232 includes an arm limit channel 237, as will be described in more detail in relation to FIGS. 14A-14B.

Figure 12A:
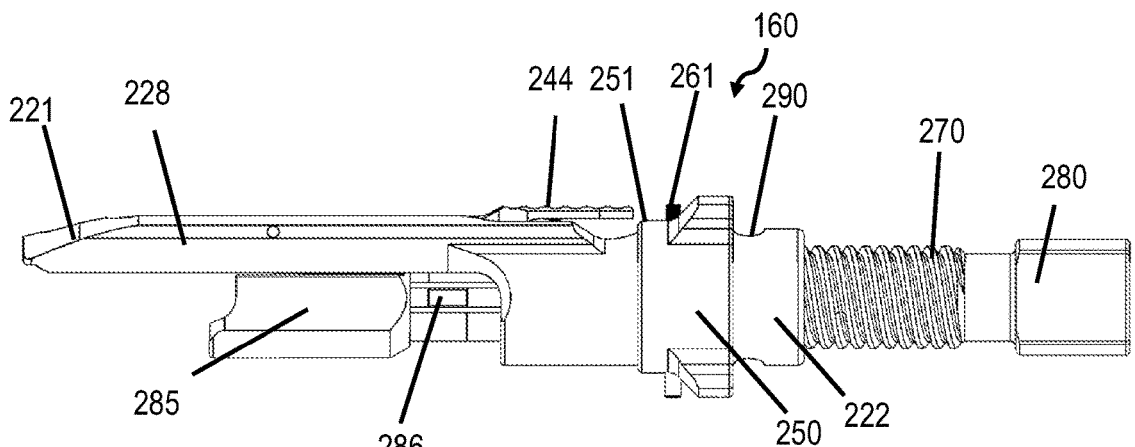
FIG. 12A is a side view that illustrates the short open-extender instrument assembly of FIG. 2 in an engaged and unlocked state.
Figure 12B:
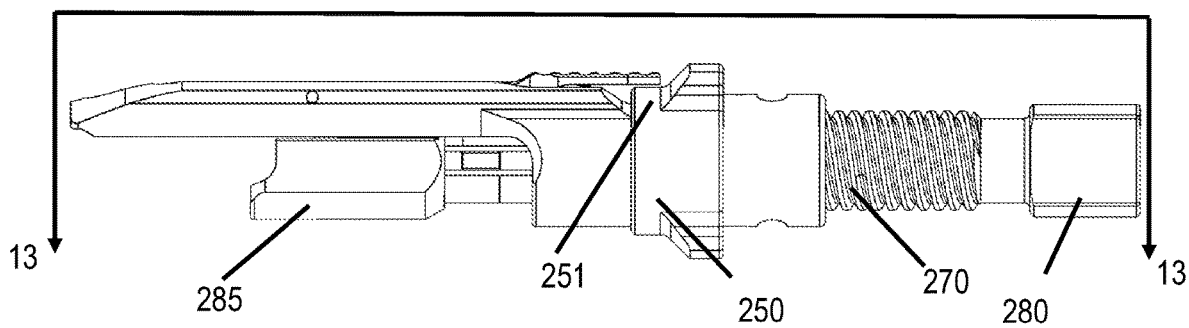
FIG. 12B is a side view that illustrates the short open-extender instrument assembly of FIG. 2 in an engaged and locked state.
Figure 13:
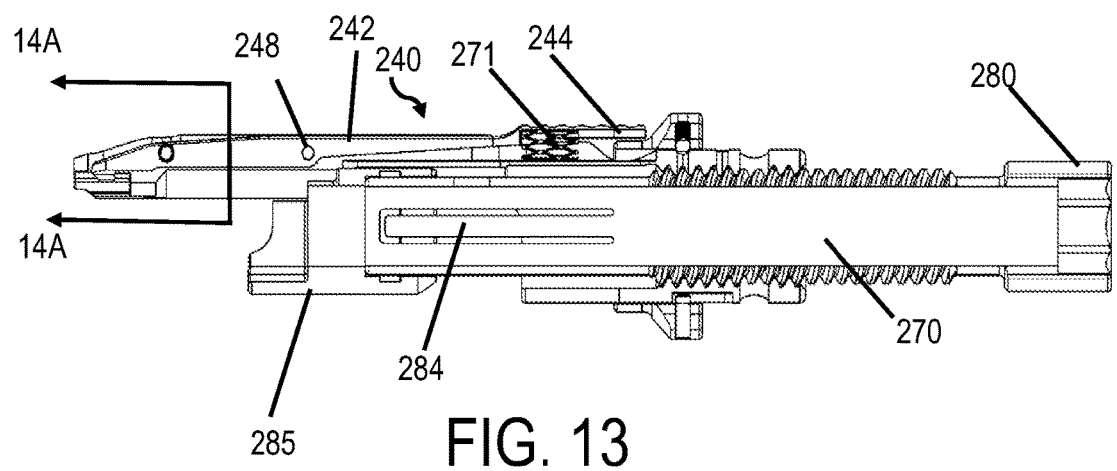
FIG. 13 is a cross-sectional view along the plane of 13-13 in FIG. 12B.

Referring also to FIGS. 12A, 12B and 13, FIG. 12A is a side view that illustrates the short open-extender instrument assembly 200 of FIG. 2 in an unlocked state; FIG. 12B is a side view that illustrates the short open-extender instrument assembly 200 of FIG. 2 in a locked state; and FIG. 13 is a cross-sectional view along the plane of 13-13 in FIG. 12B. The rocker slide lock 160 (FIG. 1A) may include the collar 250 and the at least one spring-biased bar 261. The collar 250 may have a first position that has a clearance from under the actuation tab 244, as depicted, for example, in FIG. 12A. The collar 250 may have a second position that may have a collar portion 251 located between the body member 222 and a medial side of the actuation tab 244. This collar portion 251, when under the actuation tab 244 may limit or lock the pivotal motion of the rocker assembly 240 in a direction that prevent disengagement between the head-locking projection 247 from the head.

Figure 14A:
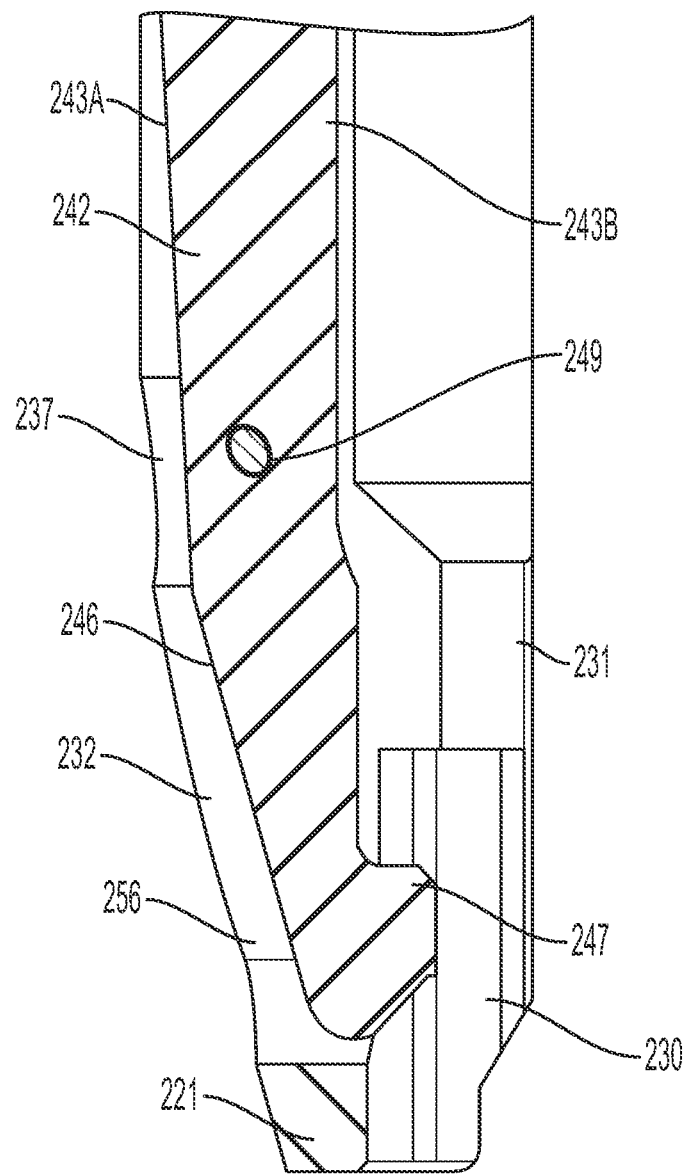
FIG. 14A is a cross-section view of along the plane 14A-14A in FIG. 13.
Figure 14B:
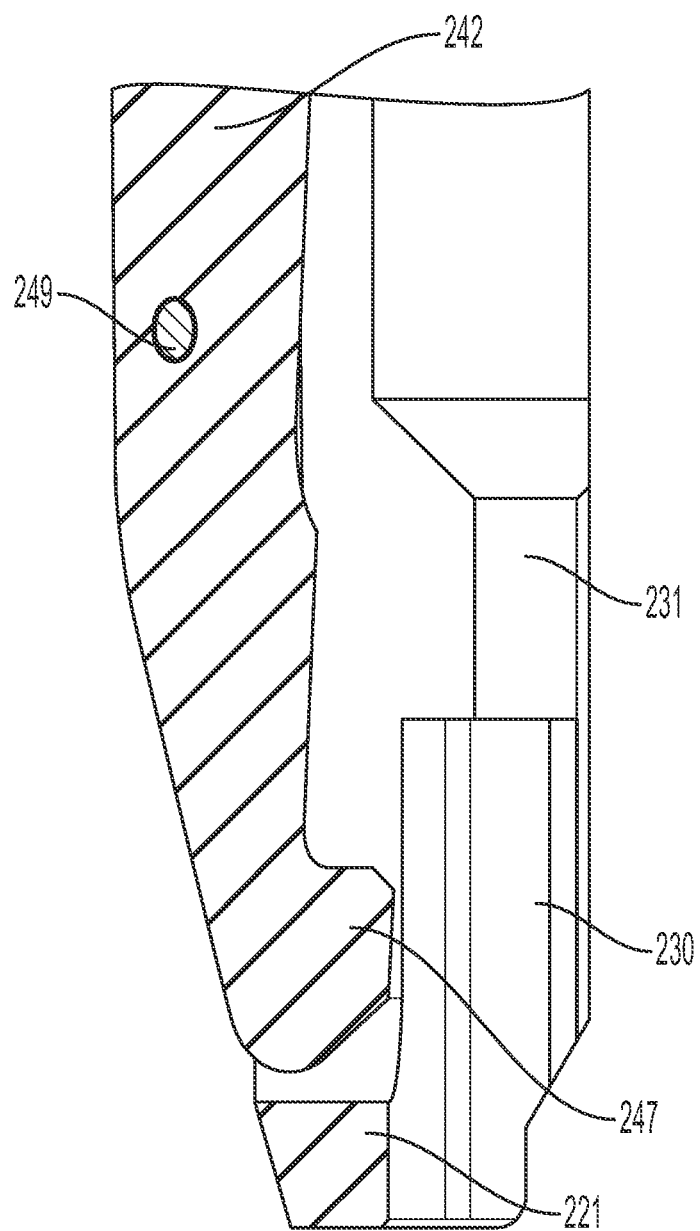
FIG. 14B is a cross-section view of along the plane 14A-14A in FIG. 13 with instrument in unlocked and disengaged position.
Figure 15:
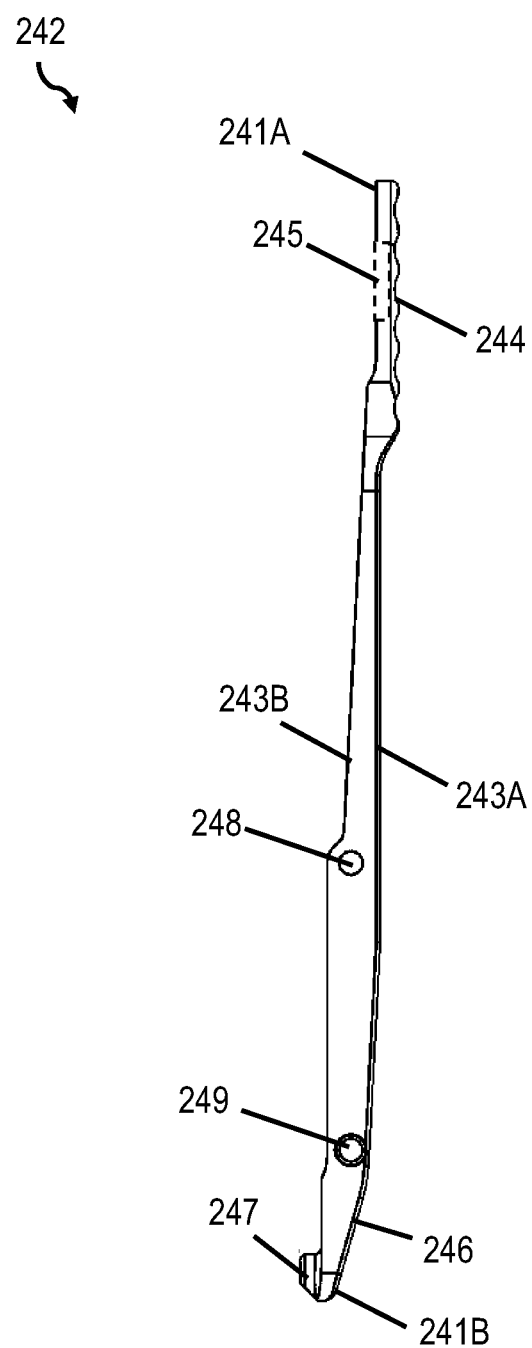
FIG. 15 is a side view that illustrates a profile of the elongated lever arm.

Referring also to FIGS. 14A-14B and 15, FIG. 14A is a cross-section view of along the plane 14A-14A in FIG. 13; FIG. 14B is a cross-section view of along the plane 14A-14A in FIG. 13 but with the instrument in unlocked and disengaged positions; and FIG. 15 is a side view that illustrates the elongated lever arm 242. When the finger or thumb presses on the actuator tab 244, the spring 271 may be compressed which allows the arm 242 to pivot so that the head-locking projection 247 may be removed from the head cavity 230.

With reference to FIG. 15, the elongated rocker assembly 240 may include an elongated lever arm 242 having a first end 241A and a second end 241B. The elongated lever arm 242 may include a first side 243A (e.g., lateral side) having a sloped end portion 246 at the second end 241B. The lever actuator tab 244 may be formed in the arm 242 on the first side 243A in proximity to the first end 241A. The elongated lever arm 242 may include a second side 243B (e.g., medial side), opposite and diametrically opposing the first side 243B. The second side 243B of the arm 242 may include a recessed cavity 245, shown in dashed lines, to hold the spring 271. The elongated lever arm 242 may include a head-locking projection 247 coupled to the second side 243B in proximity to the second end 241B. The projection 247 may be dimensioned to mate with a corresponding slot (not shown) in a bone fastener to lock or secure a head of the bone fastener, for example.

The elongated lever arm 242 may include a fulcrum 248 (FIG. 10A) coupled to the lever arm 242 in the channel 232. The pivot pin of the fulcrum 248 is shown in FIG. 11A, for example. The elongated lever arm 242 may include secondary projections 249 integrated in the arm 242 between the head-locking projection 247 and the fulcrum 248. The secondary projections 249 may be diametrically opposing and radiate from sides of the arm 242. The secondary projections 249 may radiate essentially 90° relative to a longitudinal length or axis of the arm 242. With reference to FIGS. 14A and 14B, the projections 249 fit in the limit channel 237 to limit movement of the arm 242 so that at least the lower portion of the arm 242 remains recessed or flush with the lateral side of the leg 228. The limit channel 237 limits the movement of the arm 242, such as movement of the lower portion of the arm 242 into the head cavity 230. The head-locking projection 247 may extend and project from a plane of the second side 243B. Thus, in operation, the profile of the lower portion of the arm 242 such as at least below the fulcrum 248 may not extend past a lateral side of the leg 228 when the projection is being disengaged from the head.

The leg 228 may include a first side 254A (e.g., lateral side) including a sloped portion 256 having a decreasing slope to the free end 221 of the leg 228. The leg 228 may include a second side 254B (e.g., medial side) opposite and diametrically opposing the first side 254A. The channel 232 formed in the leg has a depth such that the slopped portion 256 of the lever arm 242 is recessed within the depth of the channel 232. A length of the lever arm 242 may be recessed or flush with the first side 254A of the leg 228 and the actuation tab 244 of lever arm 242 may be raised in a plane above the first side 254A.

The short open-extender 220 may include at least one spring-biased bar 261, as depicted, for example, in FIGS. 11B, 12A and 13. The collar 250 may include diametrically opposing handles 264. A first handle 264 of the diametrically opposing handles 264 may be configured aligned with the elongated lever arm 242. The collar portion 251 extends below the handles 264.

The body member 222 may include a plurality of holes 267 arranged in succession along a longitudinal length of the body member 222. The body member 222 may include a slide hole 269 diametrically opposing the holes 267. The selective positional engagement of the spring-biased bar 261 of the collar 250 into a hole of the plurality of holes 267 may establish the locked position and unlocked position of the rocker slide lock 160 (FIG. 1A).

The at least one spring-biased bar 261 snaps the collar 250 to the first or engaged position when in the first hole and in a second disengaged position when in a different hole than the first hole. The body member 222 may include threads 266 (FIGS. 11A and 11C) formed along an interior circumferential surface. The extender's configuration may maintain a minimum profile as the elongated rocker assembly 240 moves into the engaged position and disengaged position, as shown in FIGS. 14A and 14B. In other words, a length of the arm 242 below the actuation tab 244 or below the fulcrum 248 may remain substantially recessed in or flush with the plane of the channel 232 during engaged and disengaged positions.

Referring now to FIG. 11B, the short reducer 270 may include an elongated member 272 having a top end 274 and a bottom end 276 and a removable reducer pusher 285. The elongated member 272 may include a threaded portion 278 at the upper end of the elongated member 272. The elongated member 272 below the threaded portion 278 includes a non-threaded portion. The top end 274 may include a knob 280. The knob 280 may have a larger circumference than the elongated member 272. The internal cavity of the knob 280 may include a tool fastener 282. In some embodiments, the tool fastener 282 may include a hexagonal coupler.

The elongated member 272 may include a circumference configured to fit within the body member 222 such that the threads 266 mate with threads of threaded portion 278. The elongated member 272 may also include a resilient finger 284 with a raised strip element 286 located on the finger 284. The resilient finger 284 may also include a lip 288 to lock or fasten the removable reducer pusher 285. The raised strip element 286 may be a spring press tab. When the user presses the spring press tab, the resilient finger 284 flexes to remove the lip 288 from a locked position, so that the pusher 285 may be removed (disassembled) from the elongated member 272. The resilient finger 284 engages and snaps on the reducer pusher 285, as will be described in relation to FIG. 17B. An end of the reducer pusher 285 has a rod seat 289. As the reducer pusher 285 moves down, the rod seat 289 may apply a force to push the rod (not shown) into an implanted position.

In operation, a tool (not shown) may be connected to the tool fastener 282. The reducer 270 may be configured to be turned in a body member 222 via the tool until the reducer pusher 285 of the reducer 270 engages the rod (not shown).

The extenders described herein include similar features as those described above in relation to the short open-extender 220. Any differences will be described to permit understanding. The reducer 470 (FIG. 4) described below includes similar features as reducer 270 except that the reducer pusher 285 is replaced with reducer pusher 485 (FIG. 4).

Figure 3:
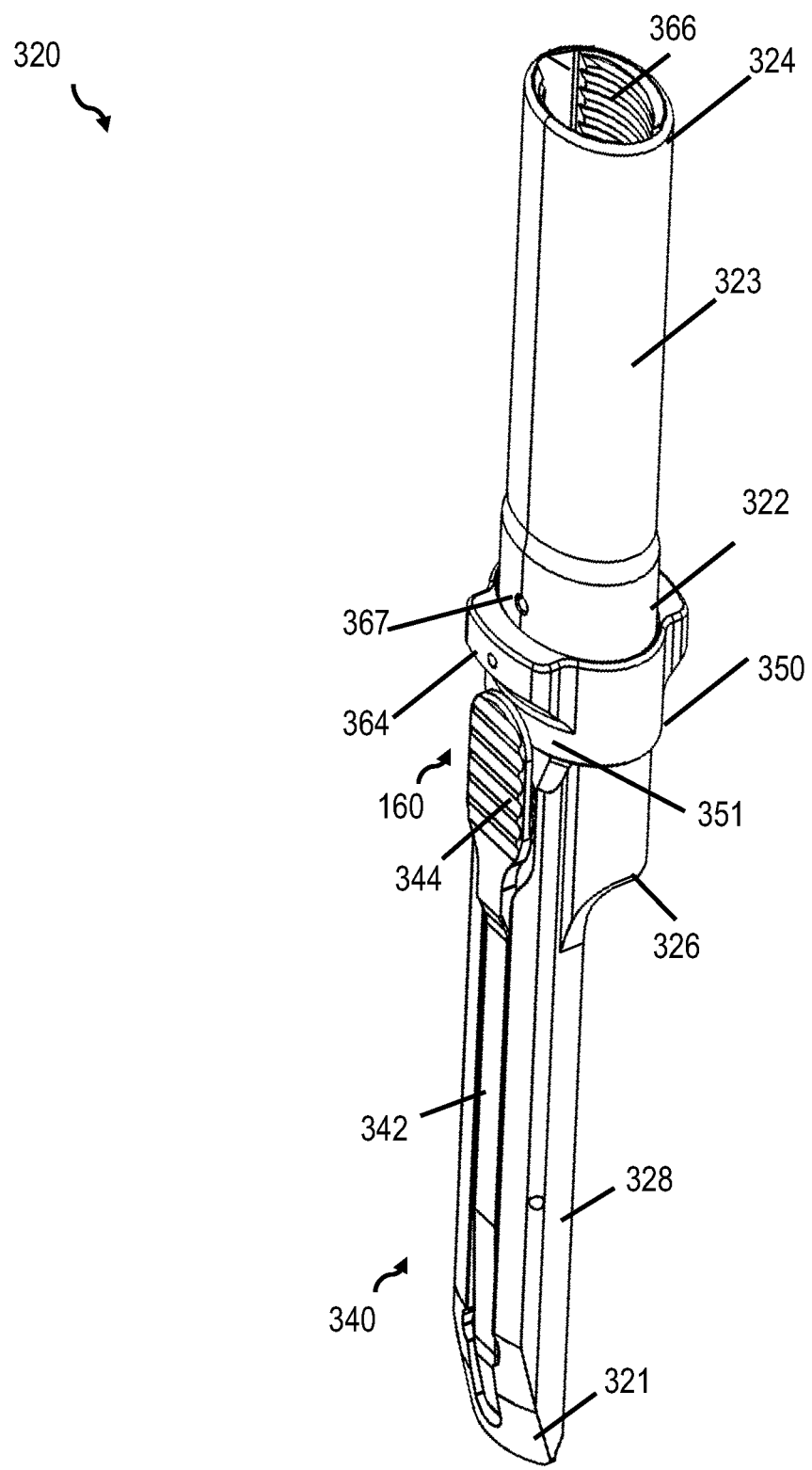
FIG. 3 is a perspective view that illustrates a long open-extender.

FIG. 3 is a perspective view that illustrates a long open-extender 320. The long open-extender 320 is similar to the short open-extender 220. Accordingly, for the sake of brevity, generally the differences will be described. The long open-extender 320 may include a body member 322 having a top end 324 and a bottom end 326. The long open-extender 320 may include a leg 328 having a first end integrated with and a leg portion extending from the body member 322. The body member 322 may be elongated and may include an elongated body member section 323. The top of the body member section 323 include threads 366.

The long open-extender 320 may include a head cavity (i.e., head cavity 230 of FIG. 10B) formed in a free end 321 of the leg 328 and configured to hold a head (not shown). A leg 328 may include channel (i.e., channel 232 of FIGS. 11A and 11C) formed along a portion of a longitudinal length of the leg 328.

The long open-extender 320 may include an elongated rocker assembly 340 pivotally coupled within the channel 232 (FIGS. 11A and 11C), with an actuation tab 444 and spring (i.e., spring 271) in proximity to the body member 322. The long open-extender 320 may include a collar 350 slidably coupled around the body member 322. A center axis of the collar 350 may be aligned with a longitudinal axis of the body member 322. The collar 350 may include diametrically opposing handles 364. A first handle 364 of the diametrically opposing handles 364 is configured to be aligned with the elongated lever arm 342 (i.e., arm 242 of FIG. 15). Thus, no further description of arm 342 is needed. The collar portion 351 extends below the handles 364.

The body member includes holes 367 for locking the collar 350 into position. The rocker slide lock 160 (FIG. 1A) may include the collar 350 and the at least one spring-biased bar (i.e., bar 261). The collar 250 may have a first position that has a clearance from under the actuation tab 244, as depicted, for example, in FIG. 12A. The collar 250 may have a second position where the collar portion 251 may be located between the body member 222 and a medial side of the actuation tab 244. This collar portion 251, when under the actuation tab 344 may limit or lock the pivotal motion of the rocker assembly 340 in a direction that would prevent disengagement between the head-locking projection (i.e., projection 247) from the head.

The operation of the long open-extender 320 is similar to the short open-extender 220. Therefore, the operation for locking and unlocking the head-locking projection (i.e., projection 247) from the head may be essentially the same as described above in relation to FIGS. 12A-12B, 13 and FIGS. 14A-14C.

FIG. 4 is a perspective view that illustrates a short closed-extender instrument assembly 400. FIG. 4 will also be described in relation to FIGS. 16A-16C. FIGS. 16A-16C are front, side and rear views of the short closed-extender instrument assembly of FIG. 4. The short closed-extender instrument assemblies 400 may include a short open-extender 420 and a short reducer 470. The short closed-extender 420 may include a body member 422 having a top end 424 and a bottom end 426. The short closed-extender 420 may include a first leg 428A and a second leg 428B that have diametrically opposing first ends integrated with and a leg portion extending from the body member 422. In general, the first leg 428A and the second leg 428B are mirror images of the other. The short closed-extender 420 may include a head cavity 430 formed in a free end 421 of the leg portions of the legs 428A and 428B. The head cavity 430 may be configured to hold a head (not shown). Since the first leg 428A and the second leg 428B are essentially the same, sometimes only one leg (i.e., leg 428A) will be described in detail. The short closed-extender 420 may include an adapter fastening element 490 formed in body member 422. The adapter fastening element 490 will be described in more detail in relation to the description of the adapter 700 (FIG. 7).

The leg 428A may have a channel 432 formed along a portion of the longitudinal length of the leg. The short closed-extender 420 may include an elongated rocker assembly 440A pivotally coupled within the channel 432 of leg 428A, with an actuation tab 444 in proximity to the body member 422. The leg 428B may have a channel 432 formed along a portion of the longitudinal length of the leg 428B. The elongated rocker assembly 440B may be pivotally coupled to channel 432 of leg 428B. The elongated rocker assemblies 440A and 440B are essentially the same as rocker assemblies 240. Thus, no further description is needed to describe the elongated rocker assemblies 440A and 440B.

The short closed-extender 420 may include an elongated rocker assembly 440A pivotally coupled within the channel 432 of leg 428A, with an actuation tab 444 in proximity to the body member 422. The short closed-extender 420 may include a collar 450 slidably coupled around the body member 422. The short closed-extender 420 may have a first position located between the body member 422 and the actuation tab 444. The portion of the collar 450 under the actuation tab 444 may limit pivotal motion of the rocker assembly 440A, 440B. The second position of the collar 450 may have a clearance from under the actuation tab 444. Example positions may be seen in FIGS. 12A-12B.

The elongated rocker assembly 440A may include an elongated lever arm 442A. The lever arm 442A is essentially the same as lever arm 242 described above in relation to FIG. 15. Thus, no further description of the arm 442A is needed. The elongated rocker assembly 440B may include an elongated lever arm 442B. The lever arm 442B may also be essentially the same as lever arm 242 described above in relation to FIG. 15. Thus, no further description of the arm 442B is needed.

The elongated lever arm 442A or 442B may include a fulcrum 448 pivotally coupled to the lever arm in the channel 432. The elongated lever arm 442A or 442B may include secondary projections (i.e., projections 249) integrated in to the arm between the projection 447 and the fulcrum 448.

The leg 428A may include a first side 454A including a sloped portion 456 having a decreasing slope to the free end 421 of the leg 428A. The leg 428A may include a second side 454B (FIG. 16B) opposite and diametrically opposing the first side 454A. The channel 432 may be essentially the same as channel 232, thus no further discussion of the channel 432 is need.

The short closed-extender 420 may include at least one spring-biased bar (i.e., bar 261 of FIG. 11B). The collar 450 may include diametrically opposing handles 464. A first handle 464 of the diametrically opposing handles 464 may be aligned with the elongated lever arm 442. The body member 422 may include a plurality of holes 467 arranged in succession along a longitudinal length of the body member 422. The rocker slide lock 160 may include the collar 450 and the at least one spring-biased bar (i.e., bar 261). The selective positional engagement of the spring-biased bar of the collar 450 into a hole of the plurality of holes 467 may establish the locked position and unlocked position. The operation of the collar 450 relative to body member 422 and the actuation tab 444 may be essentially the same as that described above in relation to FIGS. 12A-12B.

The short reducer 470 may be essentially the same as short reducer 270 previously described in relation to FIG. 11B, except that the removable reducer pusher 485 is used in lieu of pusher 285. The raised strip element 286 may be used to snap on the pusher 485 to an end of the elongated member 272 or alternatively disassembly such as for cleaning. In operation, as the reducer pusher 485 moves down between legs 428A and 428B, a force is applied by pusher 485 to push the rod (not shown) between the legs and into an implanted position. The details of the pusher 485 will be described in more detail in relation to FIG. 17A.

Figure 17A:
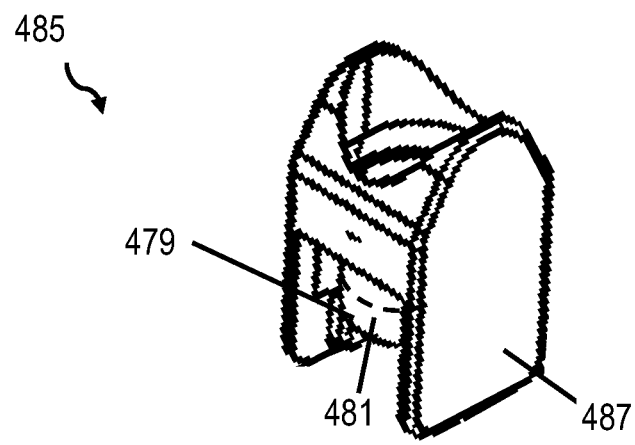
FIG. 17A is a perspective view of the second reducer pusher for the short reducer.

FIG. 17A is a perspective view of the second reducer pusher 485 for the short reducer 470. The pusher 485 includes a collar 479 configured to receive an end of the elongated element 272. The collar 479 includes a seat 481 to limit the distance the elongated element 272 can move in the collar 479. The seat 481 has a reduced diameter relative to the interior surface of the upper portion of the collar 479. The pusher 485 also includes diametrically opposing sides 487, which have a length extending below the end of collar 479. In operation, the sides 487 may be configured to apply a force to push the rod. The pusher 485 may include ribs (not shown) on the interior surface of collar 479 to latch the lip 288 (FIG. 11B) to a corresponding rib, as will be described in FIG. 17B. The spring press tabs 286 (FIG. 11B) allows the lip 288 to clear the ribs. Releasing the spring press tab 286 locks the second reducer pusher 485 to the elongated element 272.

Figure 17B:
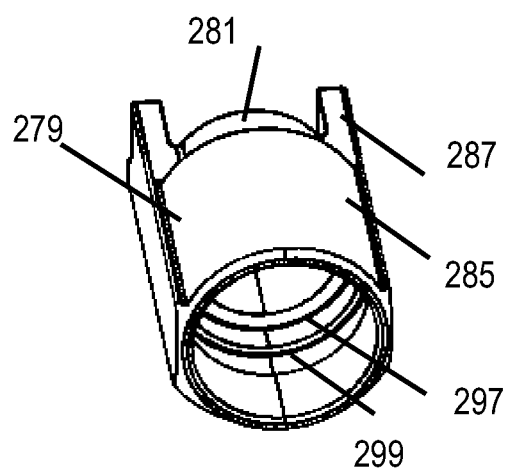
FIG. 17B illustrates top perspective view of the first reducer pusher for the short reducer.

FIG. 17B illustrates top perspective view of the first reducer pusher 285 for the short reducer 270. The first reducer pusher 285 includes a collar 279 with a seat 281 at the end of the collar 279. The seat 281 has a reduced diameter relative to the interior surface of the upper portion of the collar 279. The interior surfaces of the collar 279 have ribs 297 and 299, at least one of which may be configured to engage lip 288 to secure the pusher 285 to the elongated member 272. The pusher 285 includes sides 287 for applying a force of pressure to the rod.

FIG. 5 is a perspective view that illustrates a long closed-extender 520. The long closed-extender 520 is similar to the short closed-extender 420. Thus, for the sake of brevity, the differences will be described. The long closed-extender 520 may include a body member 522. The body member 522 may include an elongated body member section 523. The top of the body member section 523 may include threads 566. The long closed-extender 520 may include legs 528A and 528B, which are mirror images of each other. The ends of the legs form a head cavity 530.

Each leg 528A and 528B may include an elongated rocker assembly 540 with an elongated lever arm 542. The lever arm 542 is essentially the same as lever arm 242 described above in relation to FIG. 15. Thus, no further description of the arm 542 is needed.

The elongated lever arm 542 may include a fulcrum 548 pivotally coupled to the lever arm 542 in the channel 532. The elongated lever arm 542 may include secondary projections (i.e., projections 249) integrated into the arm between the projection 547 and the fulcrum 548 of the same arm.

The long closed-extender 520 may include at least one spring-biased bar (i.e., bar 261 of FIG. 11B). The collar 550 may include diametrically opposing handles 564. A first handle 564 of the diametrically opposing handles 564 may be aligned with the elongated lever arm 542. The body member 522 may include a plurality of holes 567 arranged in succession along a longitudinal length of the body member 522. The rocker slide lock 160 may include the collar 550 and the at least one spring-biased bar (i.e., bar 261). The selective positional engagement of the spring-biased bar of the collar 550 into a hole of the plurality of holes 567 may establish the locked position and unlocked position. The operation of the collar 550 relative to body member 522 and the actuation tab 544 may be essentially the same as that described above in relation to FIGS. 12A-12B.

Figure 6:
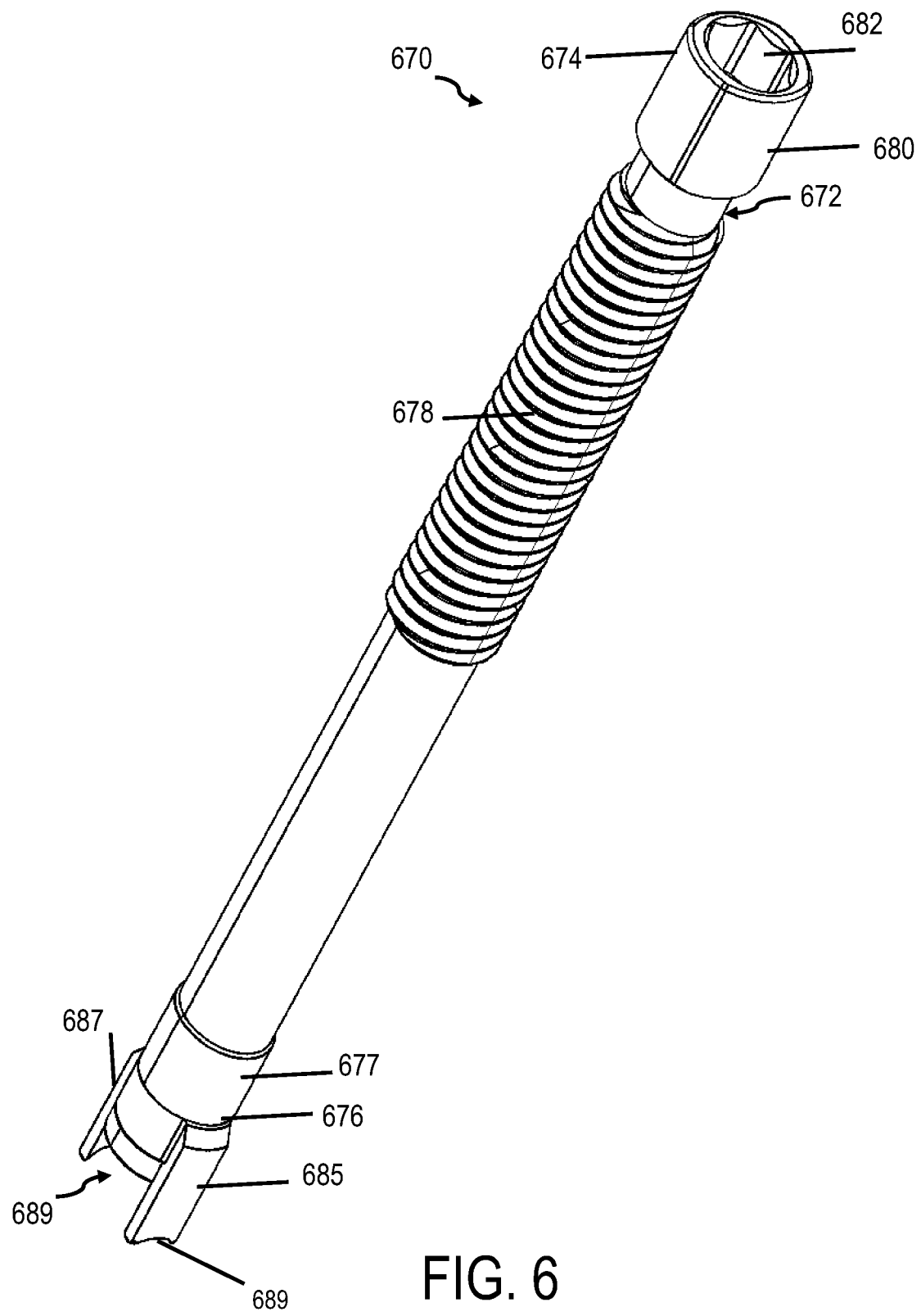
FIG. 6 is a perspective view that illustrates a long reducer.

FIG. 6 is a perspective view that illustrates a long reducer 670. The long reducer 670 may include an elongated member 672 having a top end 674 and a bottom end 676 and a removable reducer pusher 685. The elongated member 672 may include a threaded portion 678 at the upper end of the elongated member 672. The top end 674 may include a knob 680. The knob 680 may have a larger circumference than the elongated member 672. The internal cavity of the knob 680 may include a tool fastener 682. In some embodiments, the tool fastener 682 may include a hexagonal coupler. The longer reducer may allow for larger displacement of travel.

The elongated member 672 may include a circumference that fits within the body member 522 such that the threads 566 mate with threads of threaded portion 678. The reducer pusher 685 may be affixed to the end of the elongated member 672 via upper collar 677, in some embodiments. Alternately, the resilient finger arrangement described in relation to the short reducer 270 may be used. The reducer pusher 685 may have a rod seat 689. As the reducer pusher 685 moves down, the rod seat 689 may apply a force to push the rod (not shown) into an implanted position.

FIG. 7A is a perspective view that illustrates a short instrument adapter 700. FIG. 7B is a perspective view that illustrates a short instrument adapter 700 with the lever 725 and spring 726 separated. The adapter 700 may be configured to connect to open and closed type short reducers and short-extenders. In some embodiments, the adapter 700 may be part of the instrument assemblies with the short reduces and short-extenders. The adapter 700 may include a first interface body portion 720 that may include a hollow cavity dimensioned to slide on top of and fit around an outer perimeter of the handles 264 or 464 integrated in to the collar 250 or 450.

The adapter 700 may include a second interface body portion 722 integrated with the first interface body portion 720. The second interface body portion 722 may include a tubular member dimensioned to fit over and around that portion of the reducer 270 or 470 above the body member 222 or 422. The adapter 700 may include an adapter lever 725 pivotally coupled to the first interface body portion 720. The adapter lever 725 may have a first position, as shown in FIG. 7A, to engage the adapter fastening element 290 (FIG. 11A) to lock the adapter 700. The adapter lever 725 may have a second position to disengage from the adapter fastening element 290, which unlocks the adapter 700. After the adapter is unlocked, the adapter 700 may be removed from the body member 222 or 422 and the short reducer 270 or 470. The lever 725 may be pivoted about pivot hole 737 and pin 730 within lever cavity 740. The lever 725 includes an upper lever portion 734 and a bottom lever portion 735. In the first position, protrusion 736 engages hole 290 (FIG. 2) to lock the adapter 700 to the assembly 200. When the lever 725 is in a second position, the adapter 700 may be unlocked from the assembly 200 and may be removed. In the second position, a user may apply pressure to the upper lever portion 734 to pivot the lever 725 forward in in a direction away from and out of the lever cavity 740

Figure 8A:
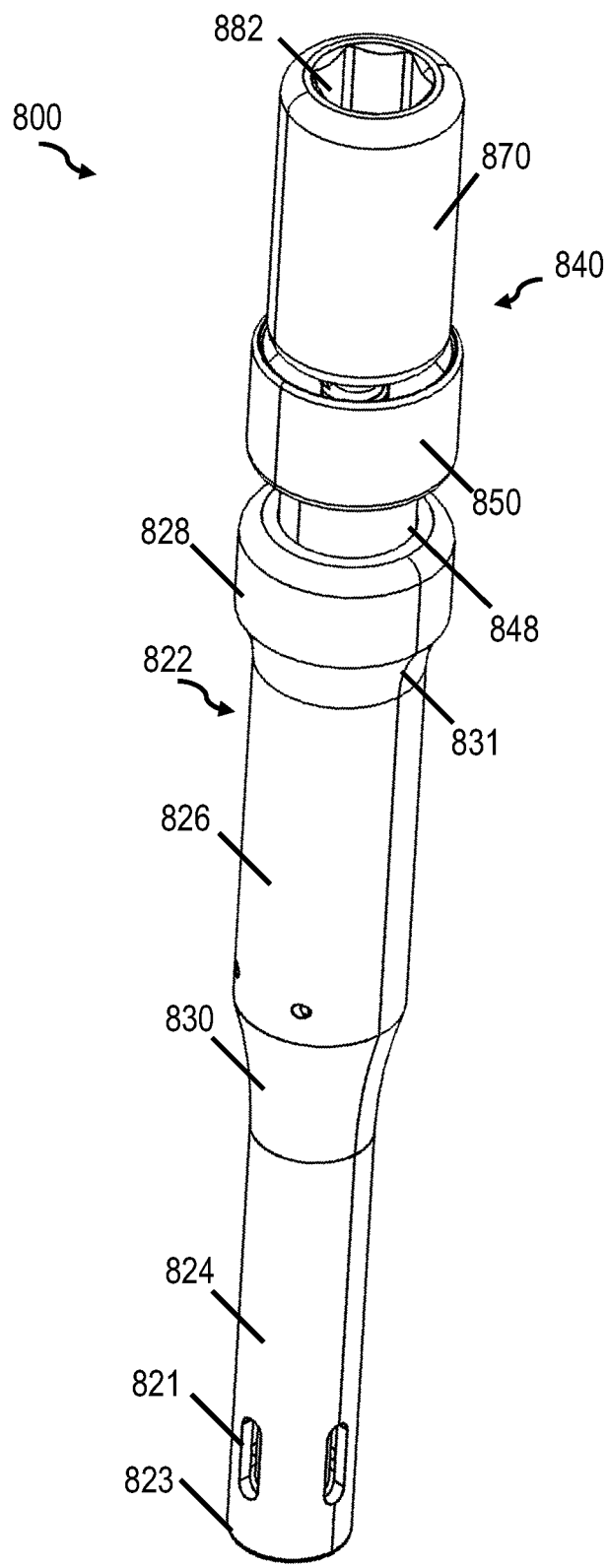
FIG. 8A is a perspective view that illustrates a shank-extender instrument assembly.

FIG. 8A is a perspective view that illustrates a shank-extender instrument assembly 800. The shank-extender instrument assembly 800 may include an outer sleeve 822 having a first portion 824, a second portion 826 and a third portion 828. The first portion 824 may have a first diameter and a second portion 826 with a second diameter. The outer sleeve 822 includes a distal end 823. The first diameter may be smaller than the second diameter. The outer sleeve 822 may include an integration zone 830, which may be gradually slopped from an end of the second portion 826 to the first portion 824. The third portion 828 may have a third diameter that is larger than the second diameter. The third portion 828 may be a knob. The outer sleeve 822 may have a second integration zone 831 between the second portion 826 and the third portion 828. A free (bottom) end of the first portion 824 may include slots 821. In operation, the outer sleeve 822 may serve as a collar.

Figure 8B:
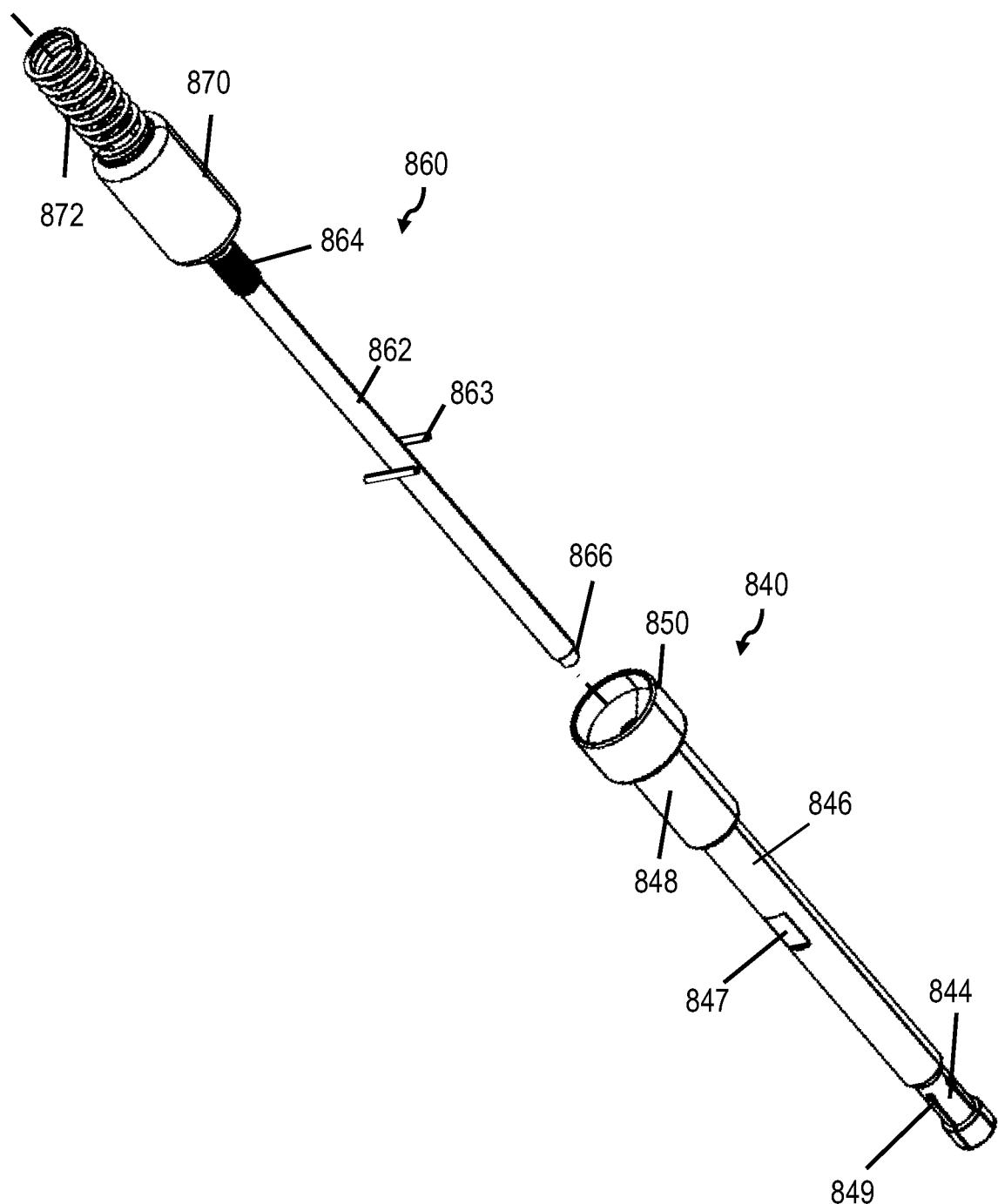
FIG. 8B is an exploded view of interior components of the shank-extender instrument assembly of FIG. 8A.

With reference also to FIG. 8B, the shank-extender instrument assembly 800 may include an middle sleeve 840 having a first portion 844, a second portion 846, a third portion 848 and a fourth portion 850. The first portion 844 may have a first diameter and a second portion 846 with a second diameter. The first diameter may be smaller than the second diameter. The third portion 828 may have a third diameter that is larger than the second diameter. The fourth portion 850 may have a fourth diameter larger than the third dimeter and may be a knob.

The first portion 844 has a plurality of slots 849 form circumferentially therearound in spaced relation. The slots 849 may be configured to align with slots 821 (FIG. 8A). The slotted first portion 844 is slotted like a collet, for example, to allow it to expand, such as when being received over a head of a bone fastener, as depicted, for example, in FIG. 20D. The first portion 844 may be integrated into a lower portion of the second portion 846 such that the distal end of the middle sleeve 840 has a diameter larger than the first diameter. The second portion 846 may include a channel 847. Instrument assembly 800 may allow derotation to be applied directly to the shank. The shank-extender instrument assembly 800 may have the ability to turn a "shank" into a fixed angle implant and manipulate directly off of the shank.

The shank-extender instrument assembly 800 may include an elongated shaft 860 having a length of shaft body 862. A top end 864 of the shaft body 862 may be threaded. The bottom end 866 of the shaft body 862 may have a reduced diameter relative to the diameter of the shaft body 862. The bottom end 866 may be configured as a connector to connect to a head of a bone fastener (FIG. 20D). The shank-extender instrument assembly 800 may include pins 863 configured to be received in channel 847.

The shaft body 862 may be configured to be received in the middle sleeve 840. The shank-extender instrument assembly 800 may include a top instrument fastener 870 to which the top end 864 may be affixed using the threads. The spring 872 may be received and housed below the third portion 848 between the middle sleeve 840 and an interior surface of the outer sleeve 822, as depicted, for example, in FIGS. 20B-20D. The top instrument fastener 870 may include a fastener element 882 (FIG. 8A) such as a hexagonal coupler. The operation of the shank-extender instrument assembly 800 will be described in more detail in relation to FIGS. 20A-20D.

Figure 9A:
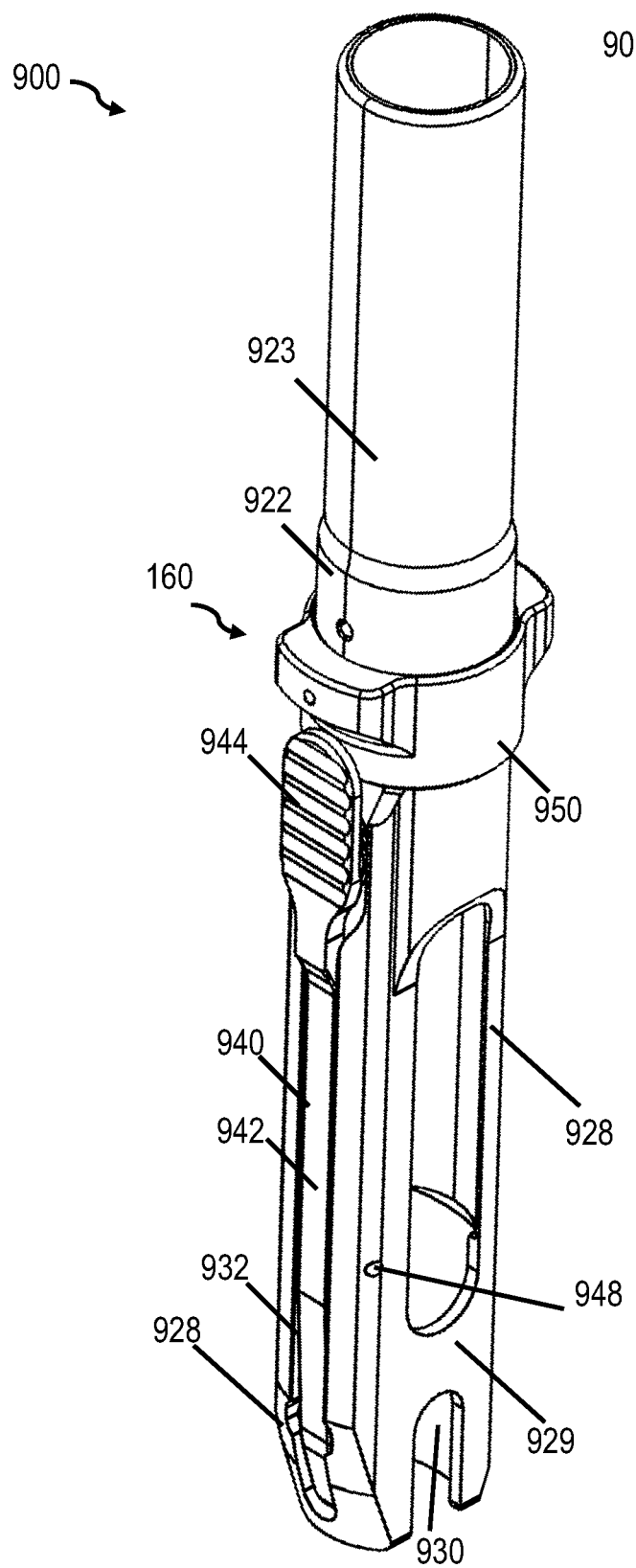
FIG. 9A is a perspective view that illustrates an apical derotator.
Figure 9B:
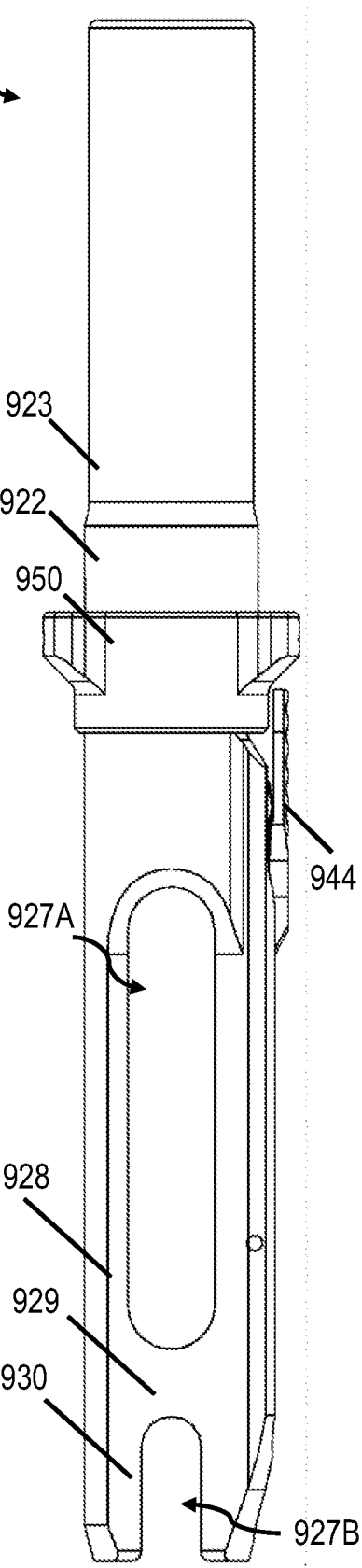
FIG. 9B is a side view that illustrates an apical derotator of FIG. 9A.
Figure 19:
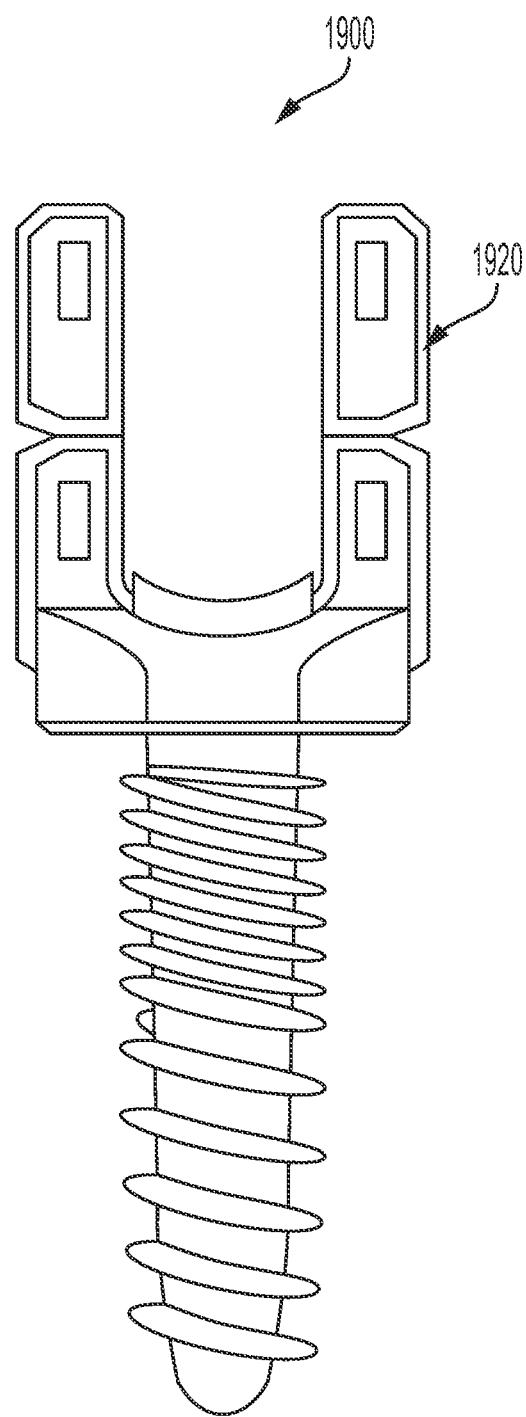
FIG. 19 is a side view that illustrates a prior art bone fastener.

FIG. 9A is a perspective view that illustrates an apical derotator 900. FIG. 9B is a side view that illustrates an apical derotator 900 of FIG. 9A. The derotator 900 is similar to a long type extender but without a reducer. The derotator 900 includes a body member 922. The body member 922 may include an elongated body member section 923. The derotator 900 may include leg 928 and support 929 that may be parallel to leg 928. The ends of the leg 928 and support 929 form a head cavity 930, such as to couple to the bone fastener 1900 (FIG. 19). The leg 928 and support 929 may be fastened together by integrated cross support 929. The apical derotator 900 includes elongated channel 927A above the cross support 929 and channel 927B below the cross support 929.

Leg 928 may include an elongated rocker assembly 940 with an elongated lever arm 942. The lever arm 942 is essentially the same as lever arm 242 described above in relation to FIG. 15. Thus, no further description of the arm 942 is needed. The elongated lever arm 942 may include a fulcrum 948 pivotally coupled to the lever arm 942 in the channel 932. The elongated lever arm 942 may include secondary projections (i.e., projections 249) integrated in the arm between the head-locking projection (i.e., projection 247) and the fulcrum 548 of the arm. The derotator 900 may have a collar 950 (i.e., collar 250) and spring-biased bar (i.e., bar 261). The rocker slide lock 160 (FIG. 1A) may include the collar 950 and the at least one spring-biased bar (i.e., bar 261). The operation of collar 950 relative to body member 922 is similar to collar 250 and body member 222, as shown and described in relation to at least FIGS. 12A and 12B. Thus, no further discussion of the collar 950 will be needed.

Figure 18:
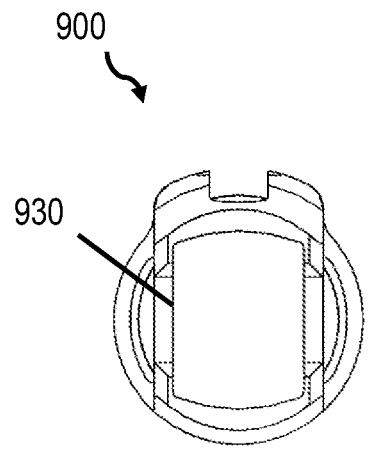
FIG. 18 is an end view of the derotator of FIG. 9A.

FIG. 18 is an end view of the derotator 900 of FIG. 9A. The derotator 900 does not have a reducer. The derotator 900 may be configured to attach to the head (i.e., head 1920) and allows for derotation manipulation. The head cavity 930 does not have a top surface (i.e. top surface 231 of FIG. 11C), so it can slide down over a reduction screw or other tabbed implant.

FIG. 19 is a side view that illustrates a prior art bone fastener 1900. The bone fastener 1900 may be a reduction screw. The reduction screw has a head 920, which may be extended relative to other bone fasteners. The reduction screw has extended tabs that allow a larger window to capture and slowly reduce the spinal rod, which can be broken off when the rod reduction is completed. An example reduction screw is described in "CD Horizon® Solera® 5.5/6.0 Spinal System," by Medtronic, Inc., copyright date 2014.

Figure 20A:
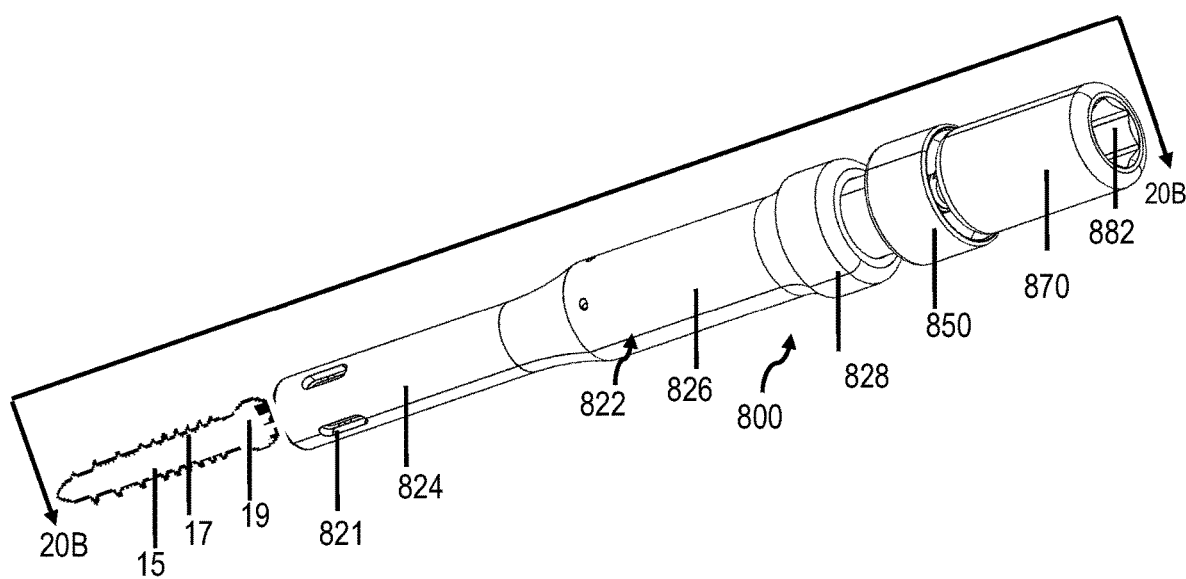
FIG. 20A is a perspective view that illustrates the shank-extender instrument assembly of FIG. 8A and a bone fastener.
Figure 20B:
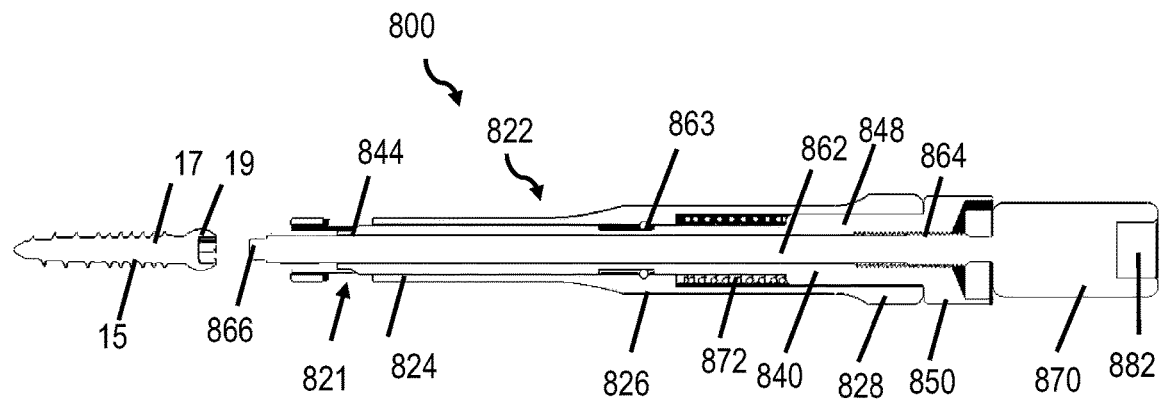
FIG. 20B is a cross-sectional view along the plane 20B-20B of FIG. 20A.
Figure 20C:
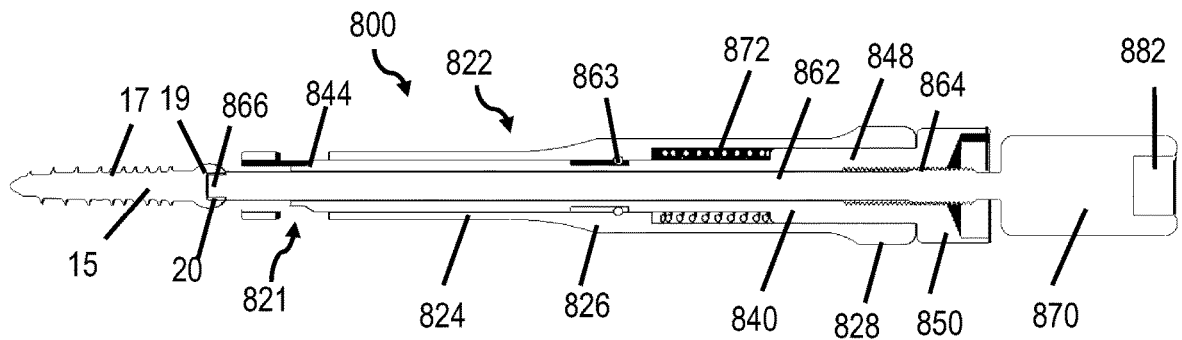
FIG. 20C is a cross-sectional view, as shown in FIG. 20B, with the bone fastener attached to the shank-extender instrument assembly in an extended position.
Figure 20D:
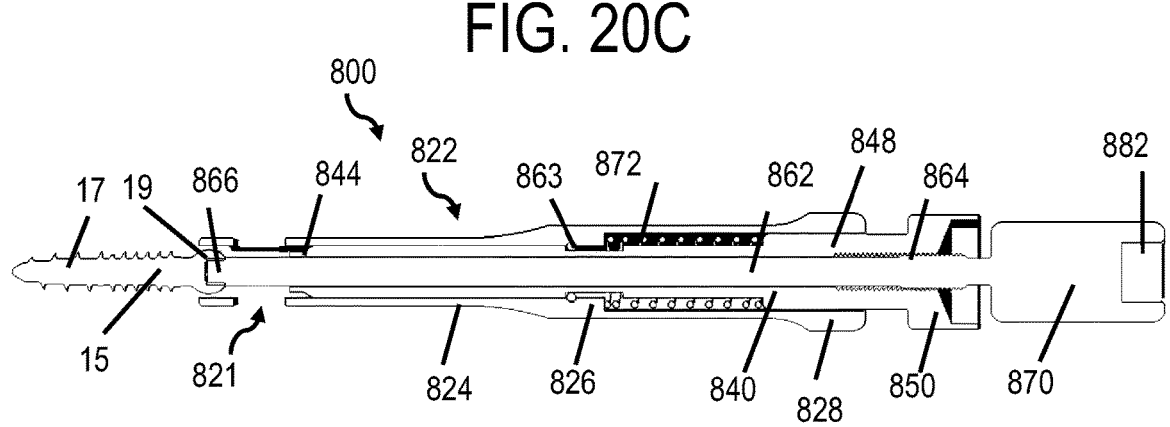
FIG. 20D is a cross-sectional view, as shown in FIG. 20B, with the bone fastener attached to the shank-extender instrument assembly in a retracted position.

FIG. 20A is a perspective view that illustrates the shank-extender instrument assembly 800 of FIG. 8A and a bone fastener 15. FIG. 20B is a cross-sectional view along the plane 20B-20B of FIG. 20A. FIG. 20C is a cross-sectional view, as shown in FIG. 20B, with the bone fastener 15 attached to the shank-extender instrument assembly 800 in an extended position. FIG. 20D is a cross-sectional view, as shown in FIG. 20B, with the bone fastener 15 attached to the shank-extender instrument assembly 800 in a retracted position. The bone fastener 15 may include a shank 17 and a head 19. The head 19 may include a notch 20 to connect to an instrument or tool. The notch 20 may be configured to provide a non-rotational connection between the head 19 and a connector (i.e., bottom end 866) of an instrument assembly 800.

In certain uses, for example, if in FIG. 20A the shank 17 is in a vertebral body and surgeon is holding instrument assembly 800, to attach the instrument assembly 800 to the shank 17, the collar (i.e., an outer sleeve 822) may be pulled back, as depicted, for example, in FIG. 20B, and the bottom end 866 (i.e., connector) may be caused to be pushed out of distal end 823 of the collar and onto the shank 17, as depicted, for example, in FIG. 20C. In this disclosure, the term "pulled back" is in the direction toward the top instrument fastener 870. The middle sleeve 840 may be slotted (like, for example, a collet) to allow it to expand and snap over the head 19 of shank 17, as disclosed, for example, in FIG. 20D. The collar (i.e., an outer sleeve 822) may be released, and a spring force from spring 872 pushes it back down to lock and/or connect the shank 17 in place.

The elongated shaft 860 can be threaded in or out to adjust the tension applied to the shank 17 when it is locked and/or connected in the instrument assembly 800. The fastener element 882 (i.e., hexagonal coupler) may be formed in the top instrument fastener 870 to allow the surgeon to use another instrument or tool to apply additional torque when adjusting the tension. Once the shank 17 is locked and/or connected into place, the surgeon can use hands or a segmental link assembly 110 and/or interlink assembly 120 or 130 as depicted, for example, in FIGS. 1A-1B, to manipulate the screws.

What is claimed is:

1. A system, comprising:
a plurality of surgical instruments of different types, each surgical instrument comprises:
an extender having
a body member having a top end and a bottom end;
a leg having a first end integrated with a leg portion extending from the body member;
a head cavity formed in a free end of the leg portion and configured to hold a head;
an elongated channel formed along a longitudinal length of the leg;
an elongated rocker assembly pivotally coupled within the elongated channel and comprising a spring actuation tab in proximity to the body member; and
a collar slidably coupled around the body member and having a first position located between the body member and the spring actuation tab such that a portion of the collar is under the spring actuation tab to limit pivotal motion of the elongated rocker assembly and a second position of the collar has a clearance from under the spring actuation tab; and
a reducer configured to interface with the extender;
wherein the extender comprises a short-open extender, a short-closed extender, a long-open extender or a long-closed extender.

2. The system of claim 1, wherein the elongated rocker assembly comprises:
an elongated lever arm having a first end and a second end, the elongated lever arm includes:
a first side having a sloped end portion at the second end of the lever arm,
a lever actuator tab formed in the arm on the first side in proximity to the first end of the arm,
a second side, opposite and diametrically opposing the first side,
a head-locking projection coupled to the second side in proximity to the second end,
a fulcrum pivotally coupled the lever arm in the elongated channel, and
secondary projections integrated into the arm between the head-locking projection and the fulcrum,
wherein the head-locking projection extends and projects from a plane of the second side.

3. The system of claim 2, wherein:
the leg comprises:
a first side including a sloped portion having a decreasing slope to the second end of the leg; and
a second side opposite and diametrically opposing the first side,
wherein:

the elongated channel formed in the leg has a depth; and the slopped portion of the lever arm is recessed within the depth of the channel, the lever arm is recessed or flush with the first side of the leg and the actuation tab raised in a plane above the first side.

4. The system of claim 1, further comprising at least one spring-biased bar, wherein:

the collar comprises:

diametrically opposing handles, a first handle of the diametrically opposing handles is configured to be aligned with the elongated lever arm; and the body member comprises:

a plurality of holes arranged in succession along a longitudinal length of the body member, the at least one spring-biased bar snaps the collar to the first position when in the first hole and in a second position when in a different hole than the first hole, and threads formed along an interior circumferential surface.

5. The system of claim 1, wherein the leg is a first leg; and further comprising a second leg having a first end integrated with and a second leg portion extending from the bottom end of the body member, the second leg diametrically opposes the first leg;

a channel formed along a portion of a longitudinal length of the second leg; and a second elongated rocker assembly pivotally coupled within the channel of the second leg and comprising a second actuation tab in proximity to the body member, wherein:

the collar slidably is coupled around the body member and the first position located between the body member and the second actuation tab such that a portion of the collar is under the second actuation tab to limit pivotal motion of the second rocker assembly and the second position has a clearance from under the second actuation tab; and a portion of the head cavity is also formed also in the second end of the second leg and configured to hold the head.

6. The system of claim 1, wherein the plurality of instruments comprises two or more of:

a derotator;

the short open-extender;

the short closed-extender;

the long open-extender; and the long closed-extender.

7. The system of claim 6, wherein the derotator comprises an apical derotator.

8. The system of claim 1, wherein the system further comprises at least one adapter configured to increase a length of the short open-extender or the short closed-extender.

9. The system of claim 8, further comprising:

a segmental link assembly comprising a segmental link and a handle configured to attach to the segmental link;

a first interlink assembly comprising a first interlink element having a first handle configured to attach to the interlink element; and a second interlink assembly comprising a second interlink element having a second handle configured to attach to the second interlink element;

wherein the first interlink element has a first size and the second interlink element has a second size different from the first size.

10. The system of claim 9, wherein the first interlink element and second interlink element are configured to attach to the adapter.

11. The system of claim 8, wherein the adapter includes a locking lever to lock to the body member at a location above the collar.

12. The system of claim 1, wherein the reducer comprises:

an elongated member having a first end, a threaded portion, a non-threaded portion and a second end;

a fastener integrated into the first end;

a resilient finger formed in the non-threaded portion;

a spring press tab formed on the resilient finger to flex the finger; and a lip at a free end of the finger.

13. The system of claim 12, wherein the reducer comprises a reducer pusher configured to be coupled to the elongated member by the lip.

14. The system of claim 1, wherein the reducer comprises:

a first short reducer configured to interface with the short open-extender, a second short reducer configured to interface with the short closed-extender, a first long reducer configured to interface with the long open-extender, or a second long reducer configured to interface with the long closed-extender.

15. The system of claim 1, further comprising a shank-extender instrument assembly.

16. The system of claim 1, further comprising a rocker slide lock having the collar constructed and arranged to lock a head-locking projection of the rocker assembly in the head nestled in the head cavity.

17. The system of claim 1, wherein:

the elongated channel comprises an arm limit channel; and the elongated rocker assembly comprises:

an elongated lever arm having a first end and a second end, the elongated lever arm includes:

a first side having a sloped end portion at the second end of the lever arm, with the actuation tab formed in the arm on the first side is in proximity to the first end of the arm, a second side, opposite and diametrically opposing the first side, a head-locking projection integrated into the second side in proximity to the second end, a fulcrum pivotally coupling the lever arm in the elongated channel, and secondary projections integrated into the arm between the head-locking projection and the fulcrum, wherein the secondary projections are coupled into the arm limit channel to limit the movement of the arm below the fulcrum within the elongated channel.

18. A method, comprising:

providing the system of claim 1;

providing a plurality of reducers;

coupling a respective one reducer to a respective one surgical instrument to form an instrument assembly with a rocker slide lock;

using the instrument assembly for reducing a rod in a head of a bone fastener; and prior to reducing the rod, locking the head with rocker slide lock.

19. The method of claim 18, further comprising:
using a respective one surgical instrument of the system of claim 1 to perform derotation.

20. A method, comprising:
using a respective one surgical instrument of the system of claim 1 to perform derotation; and
using a respective one surgical instrument of the system of claim 1 with the reducer to perform rod reduction.

21. A system, comprising:
a plurality of surgical instruments comprising at least two extenders of different types, the different types comprising a short open-extender, a short closed-extender, a long open-extender and a long closed-extender;
each of said at least two extenders comprising:
  a body member having a top end and a bottom end;
  a leg having a first end integrated with a leg portion extending from the body member;
  a head cavity formed in a free end of the leg portion and configured to hold a head;
  an elongated channel formed along a longitudinal length of the leg;
  an elongated rocker assembly pivotally coupled within the elongated channel and comprising a spring actuation tab in proximity to the body member; and
  a collar slidably coupled around the body member and having a first position located between the body member and the spring actuation tab such that a portion of the collar is under the spring actuation tab to limit pivotal motion of the elongated rocker assembly and a second position of the collar has a clearance from under the spring actuation tab; and
at least two reducers configured to interface with respective ones of the at least two extenders.

* * * * *